US010918384B2

United States Patent
Yigit et al.

(10) Patent No.: US 10,918,384 B2
(45) Date of Patent: Feb. 16, 2021

(54) SURGICAL INSTRUMENT, LOADING UNIT FOR USE THEREWITH AND RELATED METHODS

(71) Applicant: Covidien LP, Mansfield, MA (US)

(72) Inventors: Nilgun Yigit, Easton, CT (US); David Racenet, Killingworth, CT (US); Russell Estrella, Middlebury, CT (US); Gerald Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 150 days.

(21) Appl. No.: 16/136,797

(22) Filed: Sep. 20, 2018

(65) Prior Publication Data

US 2019/0015100 A1 Jan. 17, 2019

Related U.S. Application Data

(62) Division of application No. 14/660,250, filed on Mar. 17, 2015, now Pat. No. 10,092,290.

(51) Int. Cl.
*A61B 17/072* (2006.01)

(52) U.S. Cl.
CPC ...... *A61B 17/072* (2013.01); *A61B 17/07207* (2013.01); *A61B 2017/07221* (2013.01); *A61B 2017/07228* (2013.01); *A61B 2017/07271* (2013.01)

(58) Field of Classification Search
CPC ........ A61B 17/072; A61B 2017/07228; A61B 2017/07271
See application file for complete search history.

(56) References Cited

U.S. PATENT DOCUMENTS

| 3,017,637 A | 1/1962 | Sampson |
| 3,079,306 A | 2/1963 | Bobrov et al. |
| 3,499,591 A | 3/1970 | Green |

(Continued)

FOREIGN PATENT DOCUMENTS

| CA | 2773414 A1 | 11/2012 |
| CN | 1947663 A | 4/2007 |

(Continued)

OTHER PUBLICATIONS

Bollens, Renaud et al.. Laparoscopic Live Donor Right Nephrectomy: A New Technique to Maximize the Length of the Renal Vein Using a Modified Endo GIA Stapler, Dec. 5, 2006, European Urology 51 (2007), 1326-1331. (Year: 2007).*

(Continued)

*Primary Examiner* — Martin T Ton
(74) *Attorney, Agent, or Firm* — Carter, DeLuca & Farrell LLP

(57) ABSTRACT

A cartridge assembly for use with a surgical instrument including a cartridge, a longitudinal channel, a first row of slots, and a second row of slots. The cartridge has a proximal portion and a distal portion. The longitudinal channel extends between the proximal portion and the distal portion. The first row of slots is disposed on a first side of the longitudinal channel. At least one slot in the first row of slots is empty. The second row of slots is disposed on a second side of the longitudinal channel. At least one slot in the second row of slots has a staple disposed therein.

14 Claims, 25 Drawing Sheets

(56) References Cited

U.S. PATENT DOCUMENTS

| | | |
|---|---|---|
| 4,576,167 A | 3/1986 | Noiles |
| 4,633,874 A | 1/1987 | Chow et al. |
| 4,715,520 A | 12/1987 | Roehr, Jr. et al. |
| 4,819,853 A | 4/1989 | Green |
| 4,881,544 A | 11/1989 | Green et al. |
| 4,924,864 A | 5/1990 | Danzig |
| 5,014,899 A | 5/1991 | Presty et al. |
| 5,071,430 A | 12/1991 | de Salis et al. |
| 5,143,268 A | 9/1992 | Stroup, Jr. |
| 5,180,092 A | 1/1993 | Crainich |
| 5,307,976 A | 5/1994 | Olson et al. |
| 5,318,221 A | 6/1994 | Green et al. |
| 5,358,506 A | 10/1994 | Green et al. |
| 5,366,477 A | 11/1994 | LeMarie, III et al. |
| 5,379,933 A | 1/1995 | Green et al. |
| 5,389,098 A | 2/1995 | Tsuruta et al. |
| 5,397,324 A | 3/1995 | Carroll et al. |
| 5,403,312 A | 4/1995 | Yates et al. |
| 5,413,268 A | 5/1995 | Green et al. |
| 5,415,334 A | 5/1995 | Williamson et al. |
| 5,423,471 A | 6/1995 | Mastri et al. |
| 5,452,837 A | 9/1995 | Williamson, IV et al. |
| 5,465,895 A | 11/1995 | Knodel et al. |
| 5,470,008 A | 11/1995 | Rodak |
| 5,484,095 A | 1/1996 | Green et al. |
| 5,484,451 A | 1/1996 | Akopov et al. |
| 5,487,500 A | 1/1996 | Knodel et al. |
| 5,489,058 A | 2/1996 | Plyley et al. |
| 5,551,622 A | 9/1996 | Yoon |
| 5,562,241 A | 10/1996 | Knodel et al. |
| 5,597,107 A | 1/1997 | Knodel et al. |
| 5,601,573 A | 2/1997 | Fogelberg et al. |
| 5,634,584 A | 6/1997 | Okorocha et al. |
| 5,651,491 A | 7/1997 | Heaton et al. |
| 5,653,373 A | 8/1997 | Green et al. |
| 5,655,698 A | 8/1997 | Yoon |
| 5,662,258 A | 9/1997 | Knodel et al. |
| 5,662,259 A | 9/1997 | Yoon |
| 5,662,260 A | 9/1997 | Yoon |
| 5,673,841 A | 10/1997 | Schulze et al. |
| 5,680,982 A | 10/1997 | Schulze et al. |
| 5,681,330 A | 10/1997 | Hughett et al. |
| 5,794,834 A | 8/1998 | Hamblin et al. |
| 5,800,449 A | 9/1998 | Wales |
| 5,816,471 A | 10/1998 | Plyley et al. |
| 5,911,352 A | 6/1999 | Racenet et al. |
| 5,984,938 A | 11/1999 | Yoon |
| 5,988,479 A | 11/1999 | Palmer |
| 5,993,465 A | 11/1999 | Shipp et al. |
| 6,010,054 A | 1/2000 | Johnson et al. |
| 6,119,913 A | 9/2000 | Adams et al. |
| 6,131,789 A | 10/2000 | Schulze et al. |
| 6,174,309 B1 | 1/2001 | Wrublewski et al. |
| 6,241,140 B1 | 6/2001 | Adams et al. |
| 6,601,749 B2 | 8/2003 | Sullivan et al. |
| 6,607,540 B1 | 8/2003 | Shipp |
| 6,755,338 B2 | 6/2004 | Hahnen et al. |
| 6,805,273 B2 | 10/2004 | Bilotti et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,055,731 B2 | 6/2006 | Shelton, IV et al. |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,278,563 B1 | 10/2007 | Green |
| RE40,137 E | 3/2008 | Bilotti et al. |
| 7,380,696 B2 | 6/2008 | Shelton, IV et al. |
| 7,407,078 B2 | 8/2008 | Shelton, IV et al. |
| 7,434,717 B2 | 10/2008 | Shelton, IV et al. |
| 7,451,904 B2 | 11/2008 | Shelton, IV |
| 7,464,849 B2 | 12/2008 | Shelton, IV et al. |
| 7,503,474 B2 | 3/2009 | Hillstead et al. |
| 7,845,533 B2 | 12/2010 | Marczyk et al. |
| 8,348,127 B2 | 1/2013 | Marczyk |
| 10,383,628 B2 * | 8/2019 | Kang .................... A61B 90/92 |
| 2005/0070758 A1 | 3/2005 | Well et al. |
| 2005/0139636 A1 | 6/2005 | Schwemberger et al. |
| 2005/0145672 A1 | 7/2005 | Schwemberger et al. |
| 2005/0165415 A1 | 7/2005 | Wales |
| 2005/0247752 A1 | 11/2005 | Kelly et al. |
| 2005/0247753 A1 | 11/2005 | Kelly et al. |
| 2006/0144898 A1 | 7/2006 | Bilotti et al. |
| 2006/0163312 A1 | 7/2006 | Viola et al. |
| 2006/0271038 A1 | 11/2006 | Johnson et al. |
| 2007/0029364 A1 | 2/2007 | Kruszynski et al. |
| 2007/0034667 A1 | 2/2007 | Holsten et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0114261 A1 | 5/2007 | Ortiz et al. |
| 2007/0131732 A1 | 6/2007 | Holsten et al. |
| 2007/0175950 A1 | 8/2007 | Shelton, IV et al. |
| 2007/0181631 A1 | 8/2007 | Bilotti et al. |
| 2007/0219563 A1 | 9/2007 | Voegele |
| 2007/0221702 A1 | 9/2007 | Kruszynski |
| 2007/0246508 A1 | 10/2007 | Green |
| 2007/0255296 A1 | 11/2007 | Sauer |
| 2008/0027466 A1 | 1/2008 | Vitali et al. |
| 2008/0093415 A1 | 4/2008 | Bilotti et al. |
| 2008/0110958 A1 | 5/2008 | McKenna et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0272171 A1 | 11/2008 | Viola |
| 2009/0008424 A1 | 1/2009 | Green |
| 2009/0134199 A1 | 5/2009 | Heinrich et al. |
| 2010/0072257 A1 | 3/2010 | Farascioni |
| 2010/0072258 A1 * | 3/2010 | Farascioni ........... A61B 17/068 227/180.1 |
| 2010/0076459 A1 | 3/2010 | Farascioni |
| 2010/0213238 A1 | 8/2010 | Farascioni et al. |
| 2011/0071539 A1 * | 3/2011 | LeVert ............. A61B 17/32056 606/113 |
| 2012/0053406 A1 * | 3/2012 | Conlon .................. A61B 17/29 600/109 |
| 2012/0138660 A1 | 6/2012 | Shelton |
| 2014/0180281 A1 | 6/2014 | Rusin |
| 2014/0263570 A1 * | 9/2014 | Hopkins .......... A61B 17/07207 227/180.1 |

FOREIGN PATENT DOCUMENTS

| | | |
|---|---|---|
| CN | 104382626 A | 3/2015 |
| EP | 0033548 A2 | 8/1981 |
| EP | 0537498 A2 | 4/1993 |
| EP | 0600182 A2 | 6/1994 |
| EP | 1550410 A2 | 7/2005 |
| EP | 1782740 A1 | 5/2007 |
| EP | 1813209 A1 | 8/2007 |
| EP | 1908413 A1 | 4/2008 |
| EP | 1915953 A1 | 4/2008 |
| EP | 2014243 A2 | 1/2009 |
| EP | 2039308 A2 | 3/2009 |
| EP | 2090253 A2 | 8/2009 |
| EP | 2090254 A1 | 8/2009 |
| EP | 2116193 A1 | 11/2009 |
| EP | 2165662 A1 | 3/2010 |
| EP | 2583630 A2 | 4/2013 |
| EP | 2586379 A1 | 5/2013 |
| EP | 2586382 A2 | 5/2013 |
| JP | 8289895 | 11/1996 |
| WO | 0191646 A1 | 12/2001 |

(56) References Cited

FOREIGN PATENT DOCUMENTS

| WO | 03022133 A2 | 3/2003 |
| WO | 2004032761 A1 | 4/2004 |

OTHER PUBLICATIONS

Bollens, Renaud et al., Laparoscopic Live Donor Right Nephrectomy: A New Technique to Maximize the Length of the Renal Vein Using a Modified Endo GIAStapler, Dec. 5, 2006, European Urology 51 (2007), 1326-1331.
Chinese Office Action dated Apr. 1, 2015, issued in Chinese Application No. 2014100014945.
European Search Report EP 10251545.9 dated Jan. 2, 2014.
European Search Report for EP 11250468.3-2319 date of completion is Aug. 10, 2011 (3 pages).
European Search Report for EP 11250785 dated Aug. 5, 2013.
European Search Report for EP 11178544.0-1269 date of completion is Sep. 29, 2011 (3 pages).
European Search Report for EP 10251882.6-1269 date of completion is Feb. 25, 2011 (9 pages).
European Search Report for EP 11250757.9-2310 date of completion is Feb. 7, 2012 (3 pages).
European Search Report for EP 13175397 dated Aug. 22, 2013.
Japanese Office Action dated Apr. 16, 2015 issued in Japanese Appln. No. 2011-194158.
European Examination Report dated Apr. 24, 2015, issued in European Appln. No. 13155608.
European Search Report EP16160644 dated Jul. 20, 2016.
Australian Examination Report dated Aug. 10, 2020 issued in corresponding AU Appln. No. 2016200339.

\* cited by examiner

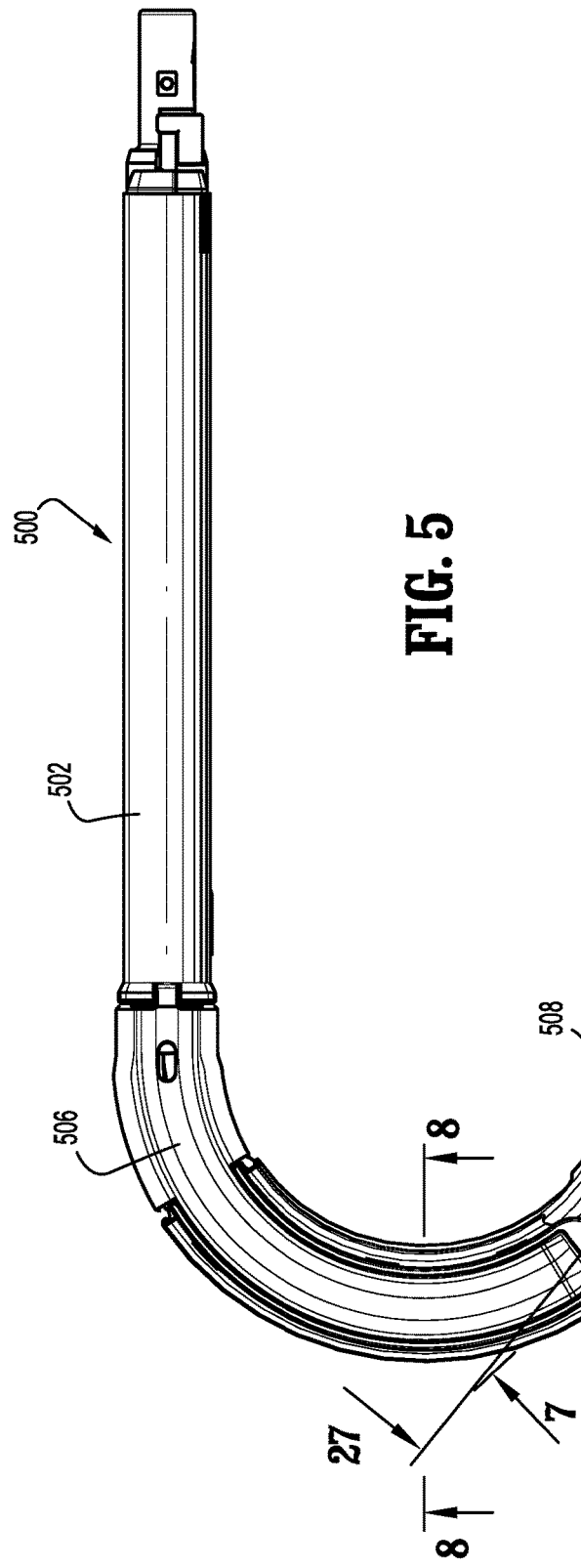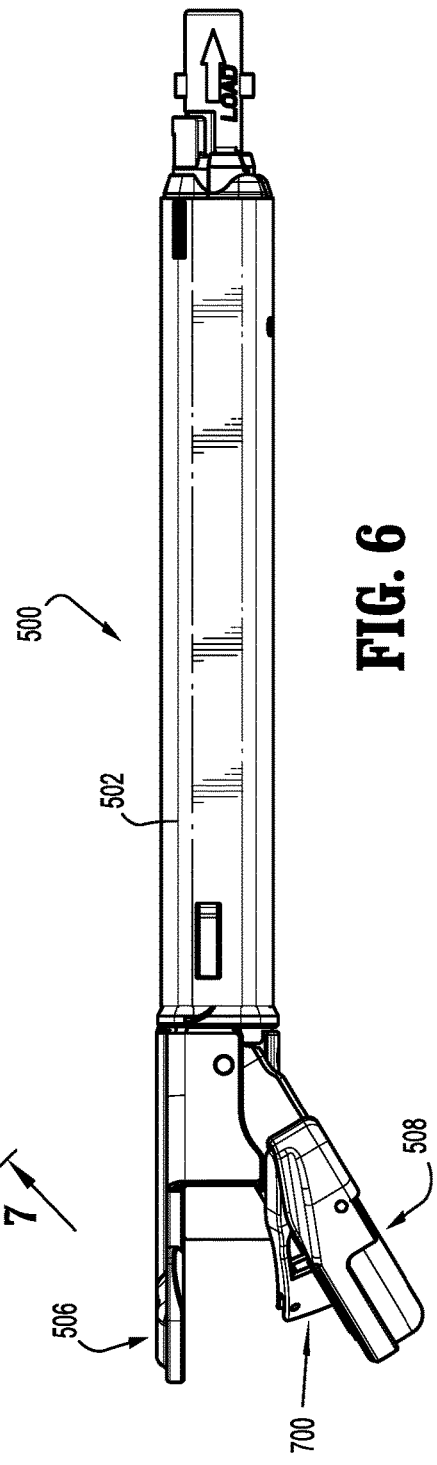

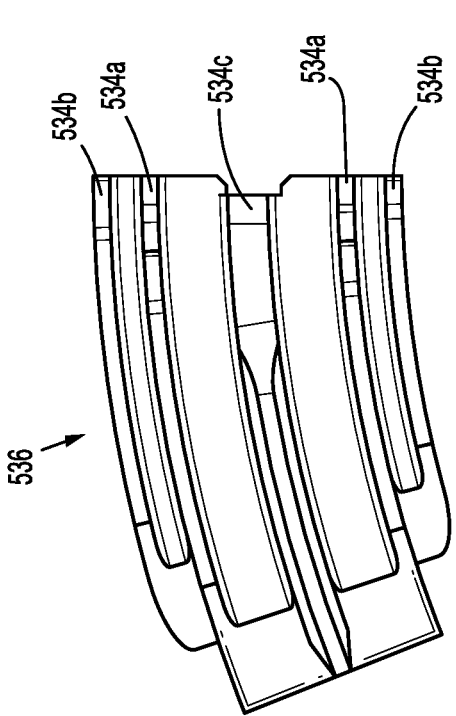
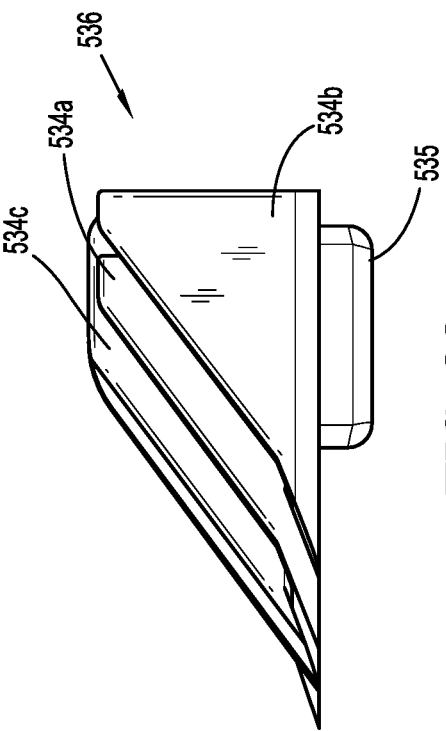
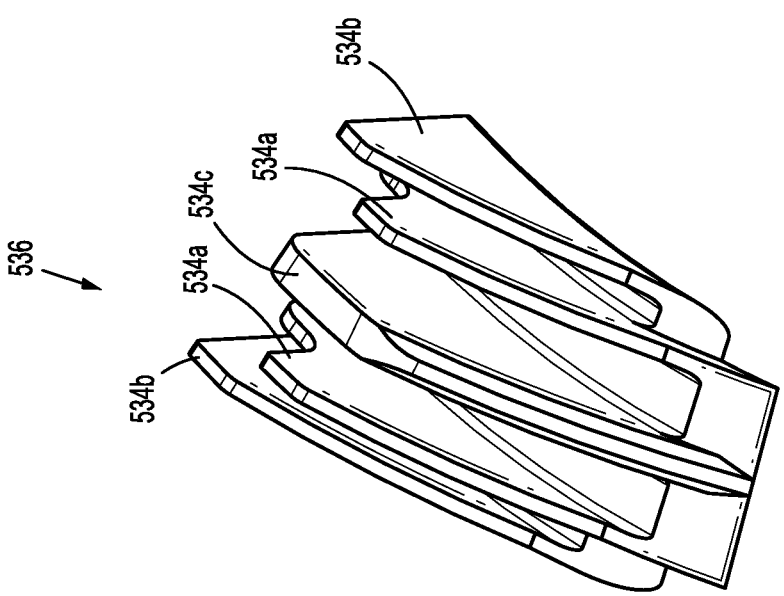

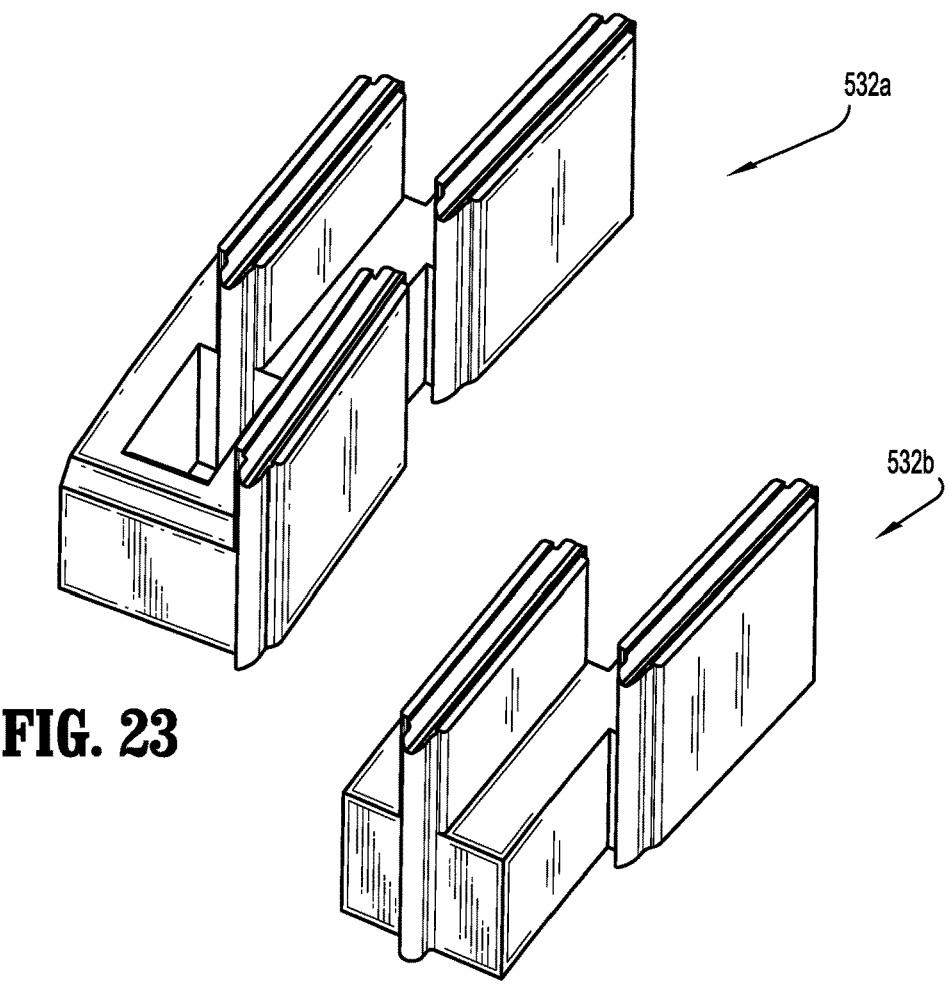
FIG. 23
FIG. 24
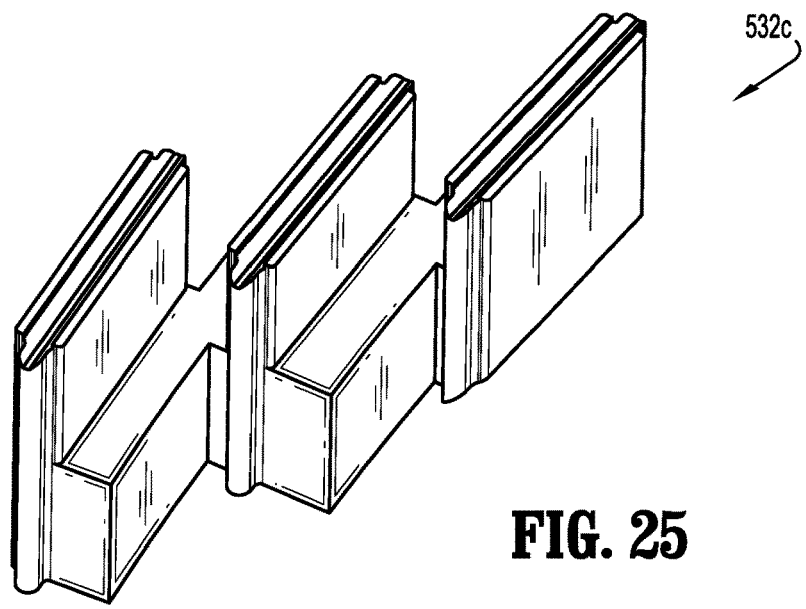
FIG. 25

SURGICAL INSTRUMENT, LOADING UNIT FOR USE THEREWITH AND RELATED METHODS

CROSS-REFERENCE TO RELATED APPLICATIONS

The present application is a Divisional Application which claims that benefit of and priority to U.S. patent application Ser. No. 14/660,250, filed on Mar. 17, 2015, the entire content of which is incorporated herein by reference.

BACKGROUND

Technical Field

The present disclosure relates generally to instruments for surgically joining tissue and, more specifically, to surgical instruments and loading units for use therewith, and to related methods of use.

Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

During use of a surgical stapling instrument, it is common for a surgeon to approximate the anvil and cartridge members to clamp tissue and subsequently fire the instrument to emplace rows of staples in the tissue. Additionally, the surgeon may use the same instrument or a separate instrument to cut the tissue adjacent or between the row(s) of staples.

SUMMARY

The present disclosure relates a cartridge assembly for use with a surgical instrument. The cartridge assembly includes a cartridge, a longitudinal channel, a first row of slots, and a second row of slots. The cartridge has a proximal portion and a distal portion. The longitudinal channel extends between the proximal portion and the distal portion. The first row of slots is disposed on a first side of the longitudinal channel. At least one slot in the first row of slots is empty. The second row of slots is disposed on a second side of the longitudinal channel. At least one slot in the second row of slots has a staple disposed therein.

In disclosed embodiments, each slot in the second row of slots includes a staple disposed therein. It is further disclosed that at least one slot in the first row of slots includes a staple disposed therein. It is also disclosed that each of the slots in the first row of slots is empty.

Disclosed embodiments of the cartridge assembly also include three rows of slots on the first side and/or the second side of the longitudinal channel. In embodiments, each row of slots of the three rows of slots on the second side of the longitudinal channel includes at least one slot having a staple disposed therein. It is disclosed that each row of slot of the three rows of slots on the first side of the longitudinal channel includes at least one slot being empty.

It is further disclosed that the cartridge defines a radius of curvature of between about 1 inch and about 2 inches, and that the first side of the longitudinal channel is shorter than the second side of the longitudinal channel.

The present disclosure also relates to a surgical instrument comprising a handle assembly, an elongated portion extending distally from the handle assembly and defining a longitudinal axis, a loading unit, and a plurality of staples. The loading unit is disposed adjacent a distal end of the elongated portion, and includes an anvil assembly and a cartridge assembly. The cartridge assembly includes a cartridge having a plurality of slots arranged in rows. Some slots of the plurality of slots include one staple of the plurality of staples disposed at least partially therein, and some slots of the plurality of slots are devoid of staples.

In disclosed embodiments, the cartridge includes a longitudinal channel extending therethrough. The plurality of slots is disposed in three rows on a first side of the longitudinal channel and in three rows on a second side of the longitudinal channel. It is disclosed that all of the slots that are devoid of staples are arranged on the first side of the longitudinal channel. It is also disclosed that the three rows of slots on the first side of the longitudinal channel include an inner row, a middle row, and an outer row. The inner row is closest to the longitudinal channel, and the outer row is farthest from the longitudinal channel. It is further disclosed that all of the slots that are devoid of staples are disposed in the middle row and the outer row on the first side of the longitudinal channel. Additionally, it is disclosed that all of the slots that are devoid of staples are disposed in the inner row and the outer row on the first side of the longitudinal channel.

In disclosed embodiments, at least one of the inner row, the middle row or the outer row includes slots that include one staple disposed therein and includes slots that are devoid of staples.

It is further disclosed that the cartridge is curved with respect to the longitudinal axis, and the first side of the longitudinal channel is shorter than the second side of the longitudinal slot.

The present disclosure also relates to a method of performing a surgical procedure comprising emplacing a first set of staples from a first side of a longitudinal channel of a surgical instrument in at least one row through tissue, emplacing a second set of staples from a second side of the longitudinal channel of the surgical instrument in at least one row through tissue, wherein the first set of staples includes more staples than the second set of staples, and advancing a knife through the longitudinal channel to cut tissue.

In disclosed embodiments, emplacing the second set of staples includes emplacing the second set of staples in a single curved row through tissue.

In certain embodiments, the second set of staples are spaced a greater distance than the first set of staples. The second set of staples can include fewer rows of staples than the first set of staples. As such, the tissue remnant having the second set of staples has more tissue unimpeded by staples and can be better disposed for testing and/or inspection.

In certain embodiments, pathological detection and/or testing of a tissue remnant stapled by the second set of staples is performed.

The pathological detection and/or testing can include testing for cancer cells.

BRIEF DESCRIPTION OF FIGURES

Various embodiments of the presently disclosed surgical instrument are disclosed herein with reference to the drawings, wherein:

FIG. 5 is a top view of the loading unit of FIGS. 3 and 4;

FIG. 6 is a side view of the loading unit of FIGS. 3-5, illustrated with a cartridge assembly in the open position;

FIGS. 18-20 are various views of an actuation sled in accordance with an embodiment of the present disclosure;

FIGS. 23-25 are perspective views of various staple pushers in accordance with embodiments of the present disclosure;

DETAILED DESCRIPTION

Figure 1:
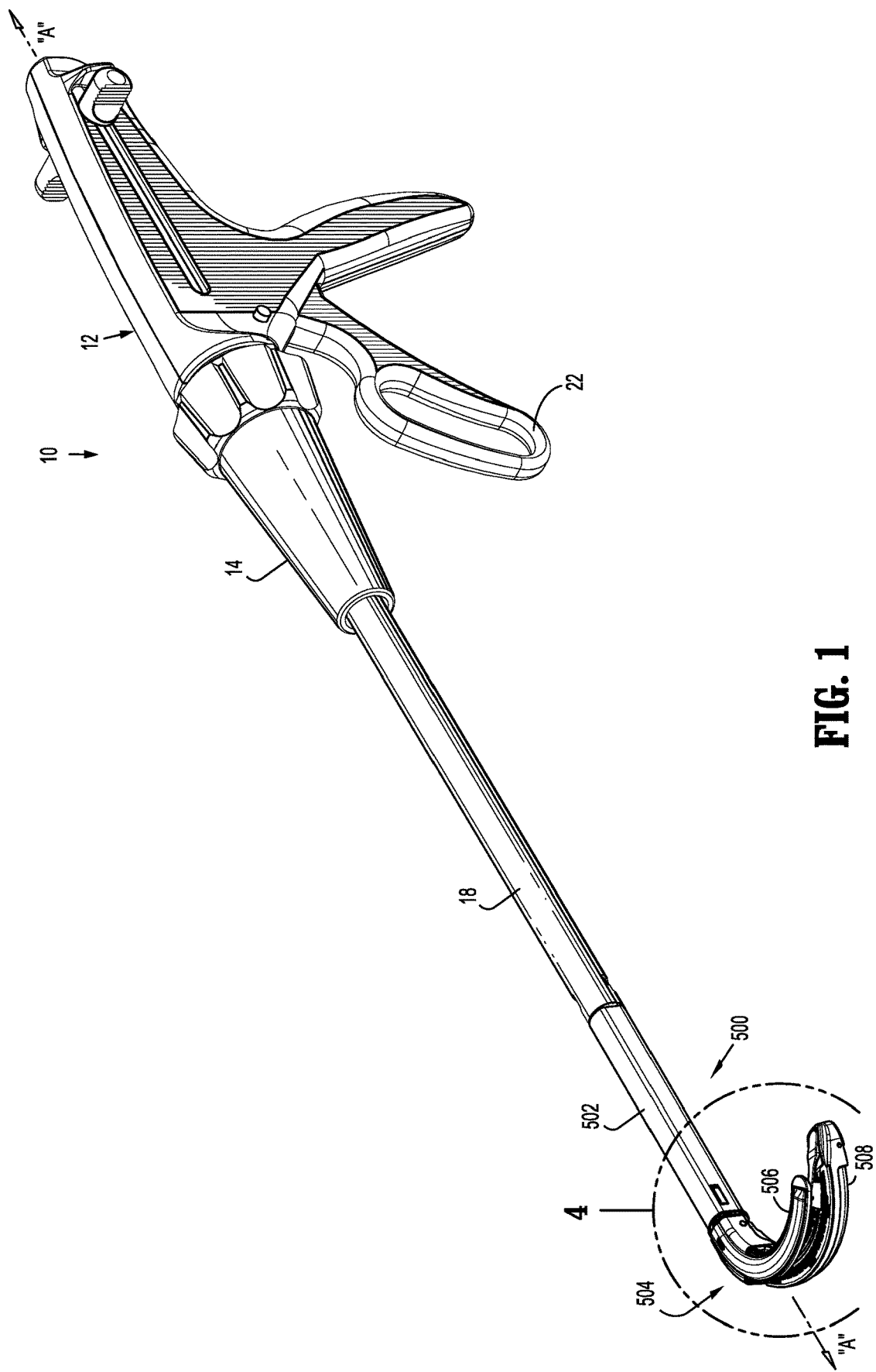
FIG. 1 is a perspective view of a surgical stapling instrument including a loading unit in accordance with the present disclosure.

Embodiments of the presently disclosed surgical instrument, and loading unit for use therewith, are described in detail with reference to the drawings, wherein like reference numerals designate corresponding elements in each of the several views. As is common in the art, the term 'proximal" refers to that part or component closer to the user or operator, e.g., surgeon or physician, while the term "distal" refers to that part or component farther away from the user.

Figure 1A:
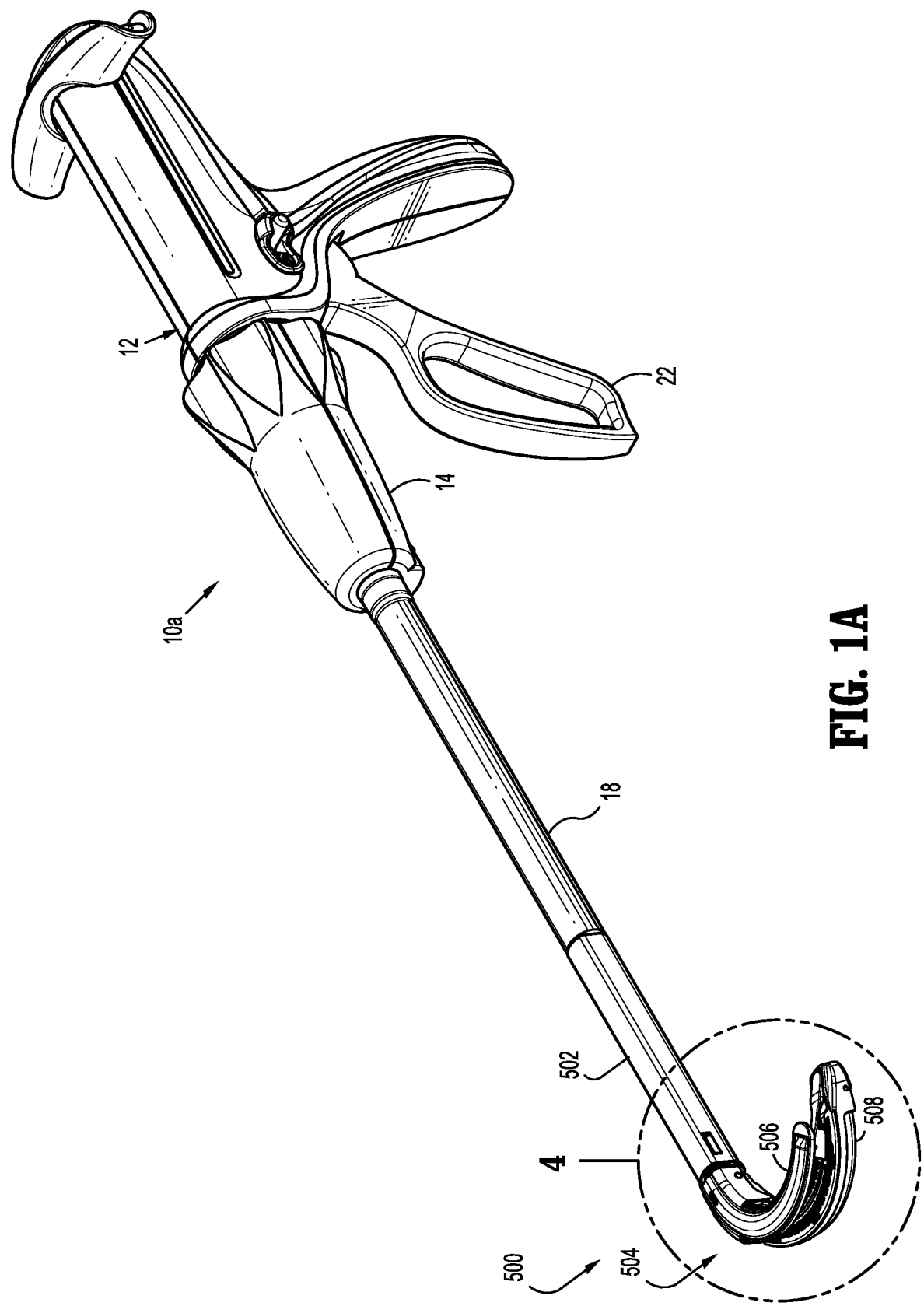
FIG. 1A is a perspective view of another type of surgical stapling instrument including the loading unit of FIG. 1 in accordance with an embodiment of the present disclosure.

A first type of surgical stapling instrument of the present disclosure is indicated as reference numeral 10 in FIG. 1. Another type of surgical stapling instrument of the present disclosure is indicated as reference numeral 10a in FIGS. 1A and 2. Additionally, while not explicitly shown, the present application also relates to surgical stapling instruments having parallel jaw members and to electrosurgical instruments used to join tissue. Collectively, all surgical instruments (including surgical stapling instruments 10 and 10a) are referred to herein as "surgical instrument" and referred to as reference numeral 10. Similarly, several features that are common to both surgical stapling instruments are collectively referred to as the same reference number (e.g., handle assembly 12, rotation knob 14, and endoscopic portion 18). Further details of an endoscopic surgical stapling instrument are described in detail in commonly-owned U.S. Pat. No. 6,953,139 to Milliman et al., the entire contents of which are hereby incorporated by reference herein.

A loading unit 500 (e.g., a disposable loading unit or a reusable loading unit) for use with surgical instrument 10 is shown in FIGS. 3-10 and 28-30. Loading unit 500 is attachable to an elongated or endoscopic portion 18 of surgical instrument 10, e.g., to allow surgical instrument 10 to have greater versatility. Loading unit 500 may be configured for a single use, and/or may be configured to be used more than once. Examples of loading units for use with a surgical stapling instrument are disclosed in commonly-owned U.S. Pat. No. 5,752,644 to Bolanos et al., the entire contents of which are hereby incorporated by reference herein. The loading unit shown includes a proximal body portion that is attachable to an elongated portion of a surgical instrument having a handle assembly. However, the tool assembly can be incorporated in a surgical instrument in which a staple cartridge is removable and replaceable and does not include a detachable portion of the elongated portion of the instrument. Furthermore, the tool assembly can be incorporated in a reload that is attachable to a powered surgical handle or system, or to a robotic system.

Loading unit 500 includes a proximal body portion 502 and a tool assembly 504. Proximal body portion 502 defines a longitudinal axis "A-A," and is releasably attachable to a distal end of elongated body portion 18 of surgical instrument 10. Tool assembly 504 includes a pair of jaw members including an anvil assembly 506 and a cartridge assembly 508. One jaw member is pivotal in relation to the other. In the illustrated embodiments, cartridge assembly 508 is pivotal in relation to anvil assembly 506 and is movable between an open or unclamped position (e.g., FIGS. 4 and 6) and a closed or approximated position (e.g., FIG. 8). Cartridge assembly 508 is urged in the open position via a biasing member, e.g., a pair of compression springs 533 disposed between anvil cover 510 and cartridge 518 (see FIG. 10).

Figure 10:
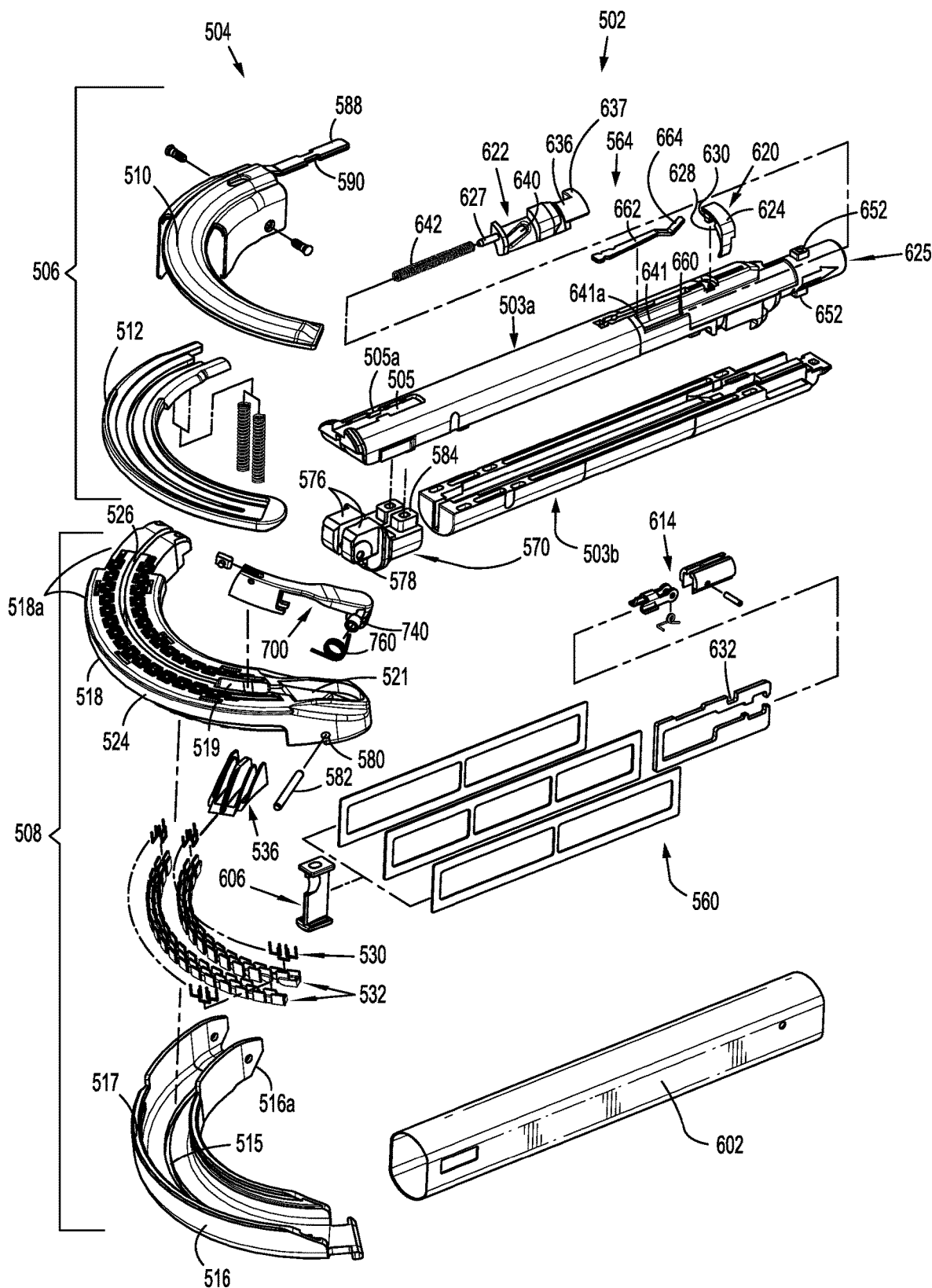
FIG. 10 is a perspective assembly view of the loading unit of FIGS. 3-9.

With reference to FIGS. 1 and 10, for example, tool assembly 504 includes anvil assembly 506 and cartridge assembly 508. As shown, each of anvil assembly 506 and cartridge assembly 508 is longitudinally curved. That is, anvil assembly 506 and cartridge assembly 508 are curved with respect to the longitudinal axis "A-A" defined by proximal body portion 502. As used herein with respect to curved parts of the surgical instrument 10 of the present disclosure, the term "distal," which typically refers to that part or component of the instrument that is farther away from the user, refers to the portion of the curved part that is farthest along an axis that follows the curve of the curved part. That is, while an intermediate portion of a curved part may be farther from the user during use, the portion of the curved part that is farthest along its axis is considered "distal."

In disclosed embodiments, the radius of curvature of both anvil assembly 506 and cartridge assembly 508 is between about 1.00 inches and about 2.00 inches, and in particular, may be approximately 1.40 inches. The curved jaw members, as compared to straight jaw members, may help facilitate access to lower pelvis regions, e.g., during lower anterior resection ("LAR"). Additionally, the inclusion of curved jaw members may allow increased visualization to a surgical site and may also allow more room for a surgeon to manipulate target tissue or the jaw members themselves.

Figure 8:
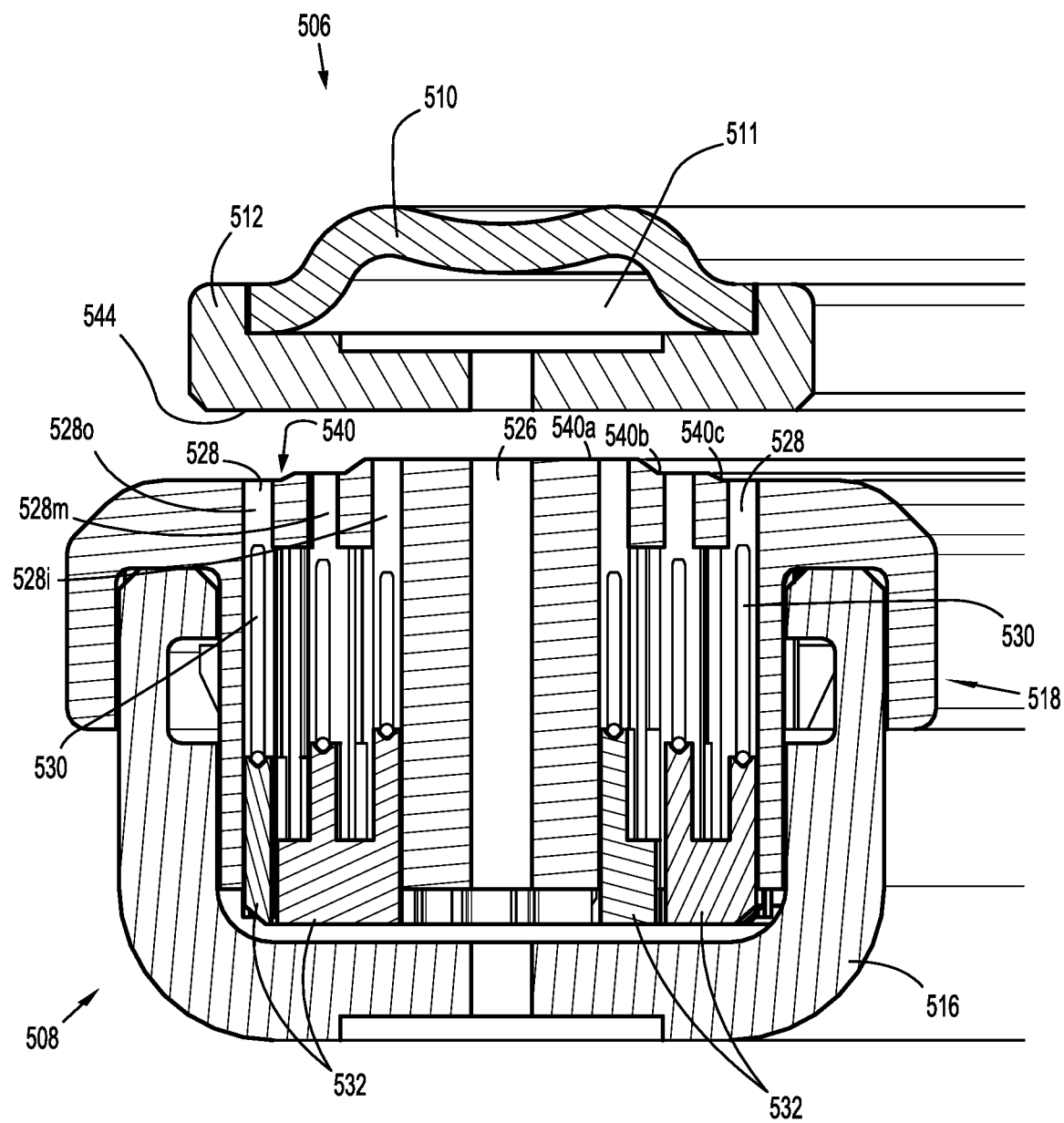
FIG. 8 is a transverse cross-sectional view of the loading unit of FIGS. 3-7.
Figure 9:
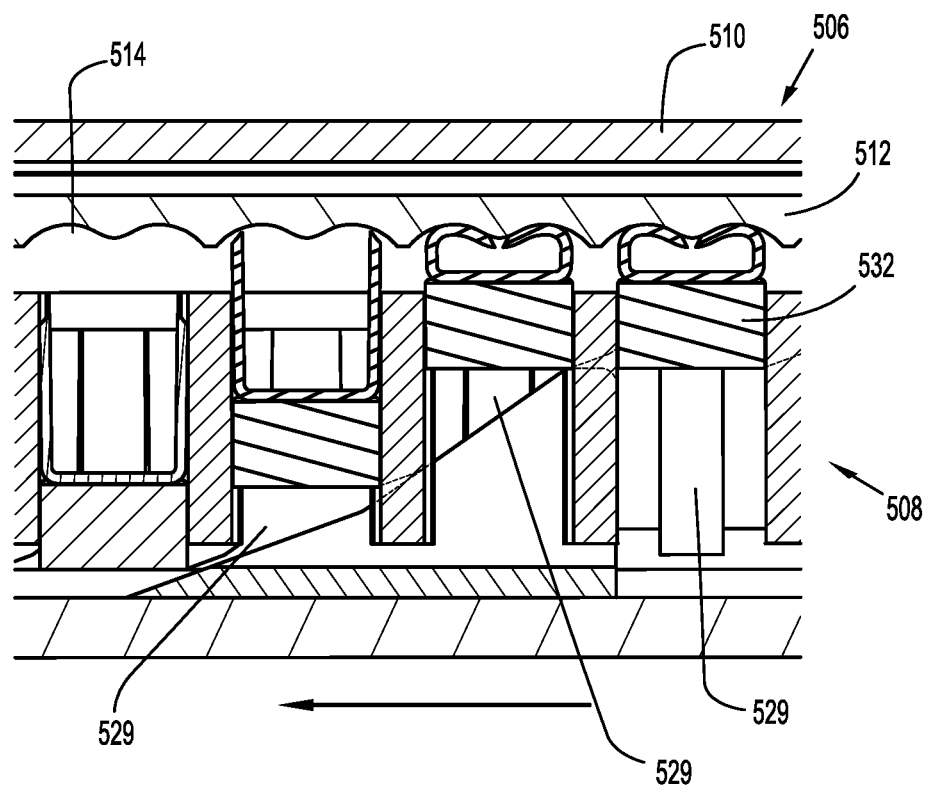
FIG. 9 is a longitudinal cross-sectional view of a portion of the loading unit of FIGS. 3-8.

With reference to FIG. 10, anvil assembly 506 includes a longitudinally curved anvil cover 510 and a longitudinally curved anvil plate 512, which includes a plurality of staple forming depressions 514 (FIG. 9). In disclosed embodiments, the radius of curvature of both anvil cover 510 and anvil plate 512 is between about 1.00 inches and about 2.00 inches, and in particular, may be approximately 1.40 inches. Anvil plate 512 is secured to an underside of anvil cover to define a channel 511 (FIG. 8) between plate 512 and cover 510. When tool assembly 504 is in the approximated position (FIG. 8), staple forming depressions 514 are positioned in juxtaposed alignment with cartridge assembly 508.

Cartridge assembly 508 includes a longitudinally curved channel or carrier 516 which receives and supports a longitudinally curved cartridge 518. The cartridge 518 can be attached to the channel or carrier by adhesives, a snap-fit connection, or other connection. In disclosed embodiments, the radius of curvature of both carrier 516 and cartridge 518 is between about 1.00 inches and about 2.00 inches, and in particular, may be approximately 1.40 inches. Cartridge 518 includes a pair of support struts 524 which rest on sidewalls 517 of carrier 516 to stabilize cartridge 518 on carrier 516. Support struts 524 also set the height or location of cartridge 518 with respect to anvil plate 512. An external surface of carrier 516 includes an angled cam surface 516a.

Figure 7:
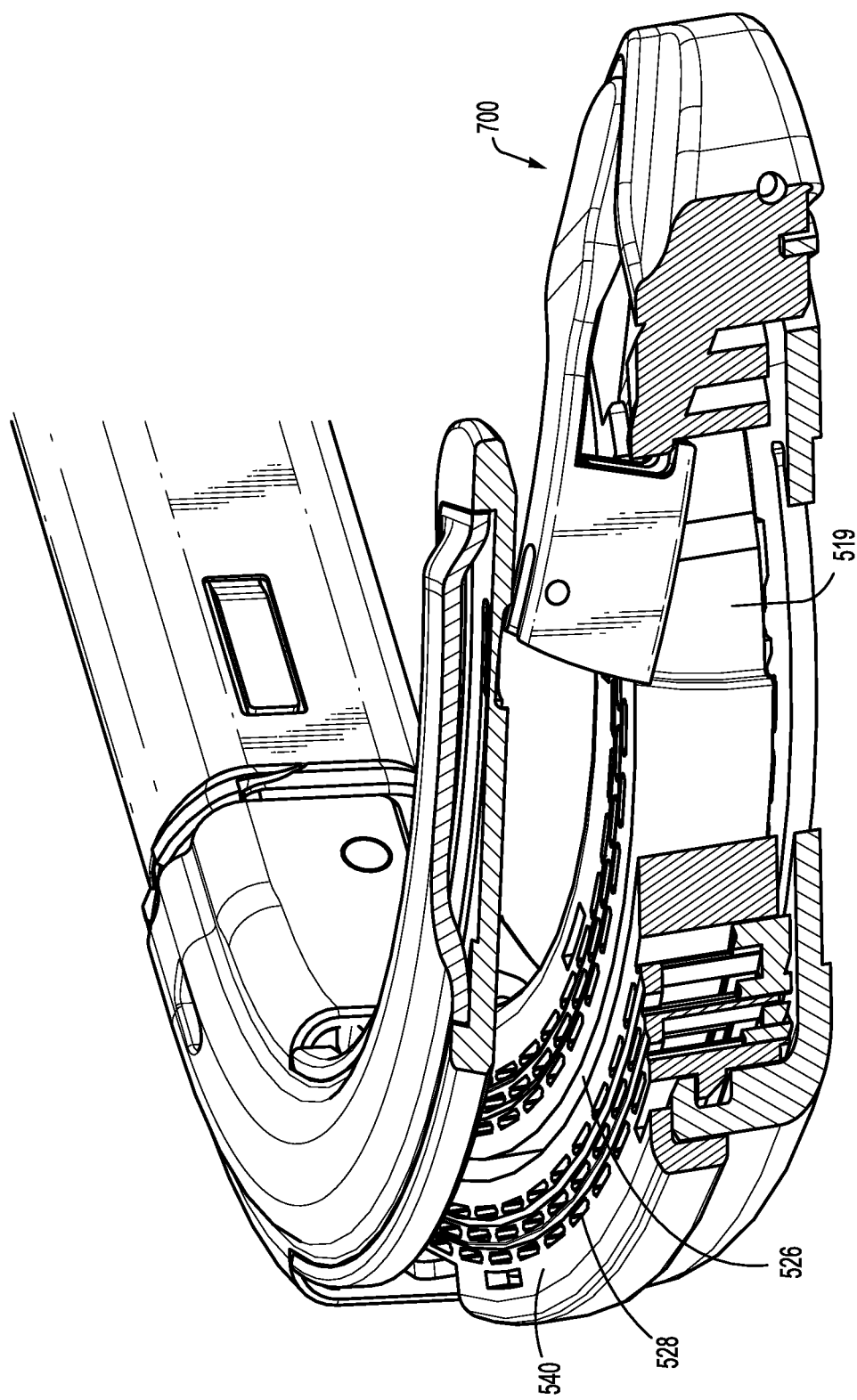
FIG. 7 is a perspective, partial cross-sectional view of the loading unit of FIGS. 3-6.

Cartridge 518 defines a plurality of laterally spaced staple retention slots 528, which are configured as holes in tissue contacting surface 540 (see FIG. 7). Each slot 528 is configured to receive a staple 530 therein. Cartridge 518 also defines a plurality of cam wedge slots 529 (see FIG. 9) which accommodate staple pushers 532 and which are open on the bottom (i.e., away from tissue contacting surface 540) to allow a longitudinally curved actuation sled 536 to pass therethrough.

Staple cartridge 518 includes a central longitudinally curved slot channel or channel 526, and three longitudinally curved rows of staple retention slots 528 positioned on each side of curved longitudinal channel 526 (see FIGS. 7 and 8). In disclosed embodiments, the radius of curvature of both channel 526 and pusher 532 is between about 1.00 inches and about 2.00 inches, and in particular, may be approximately 1.40 inches. More specifically, actuation sled 536 passes through cam wedge slots 529 and forces staple pushers 532 towards respective staples 530. The staples are then forced out of their respective staple retention slots 528.

Figure 21:
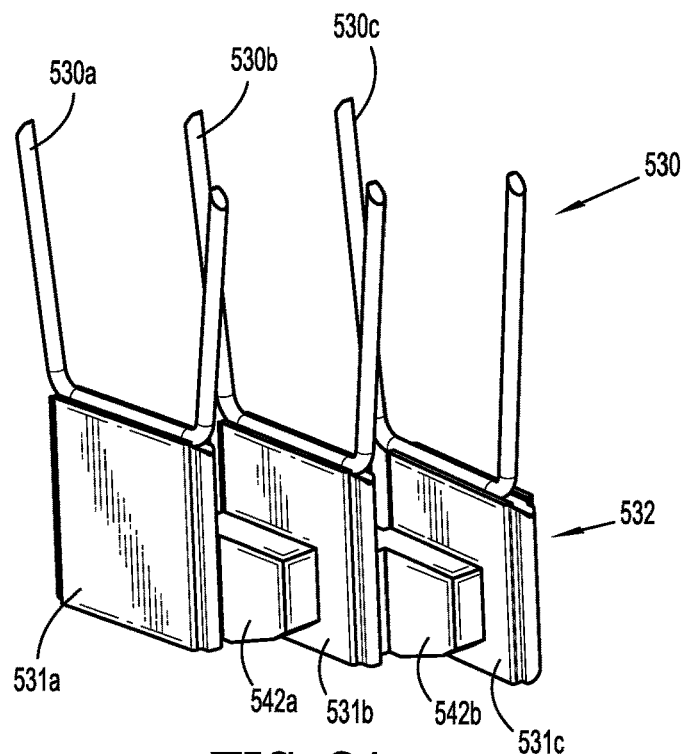
FIGS. 21 and 22 are perspective views of staples and staple pushers in accordance with embodiments of the present disclosure.
Figure 22:
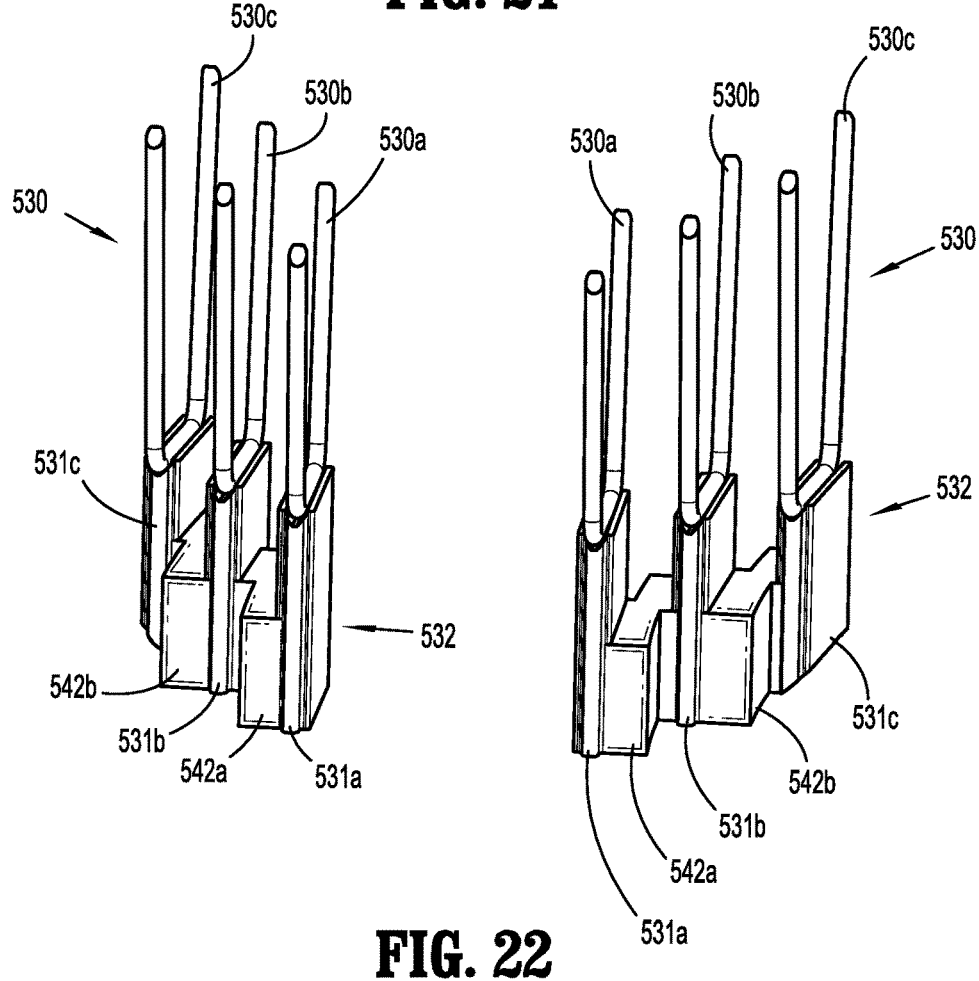
Figure 27:
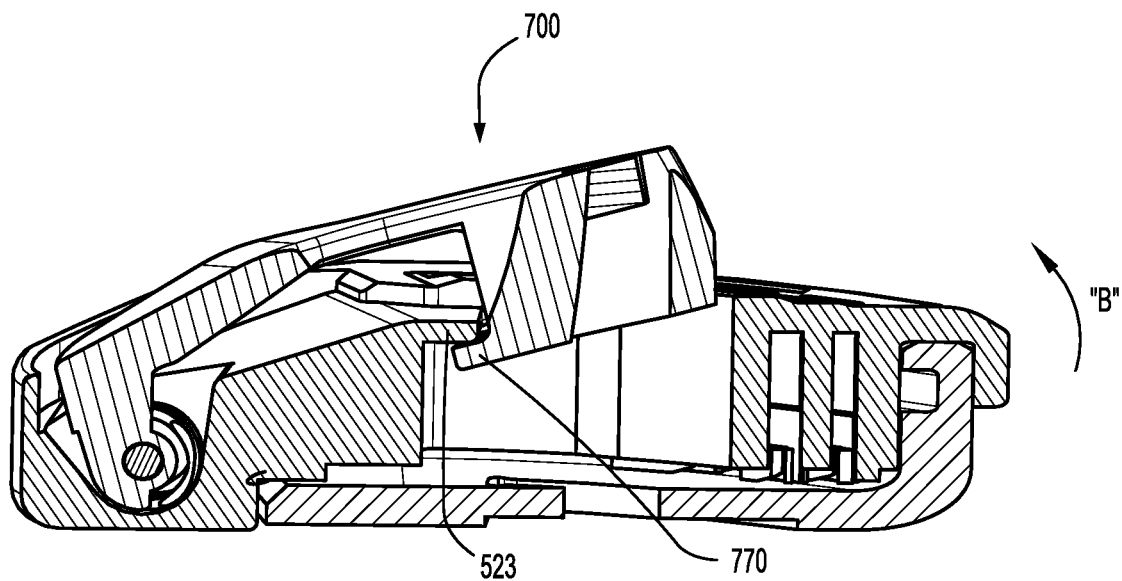
FIG. 27 is a cross-sectional view of the tissue stop of FIG. 26 coupled to the loading unit.
Figure 26:
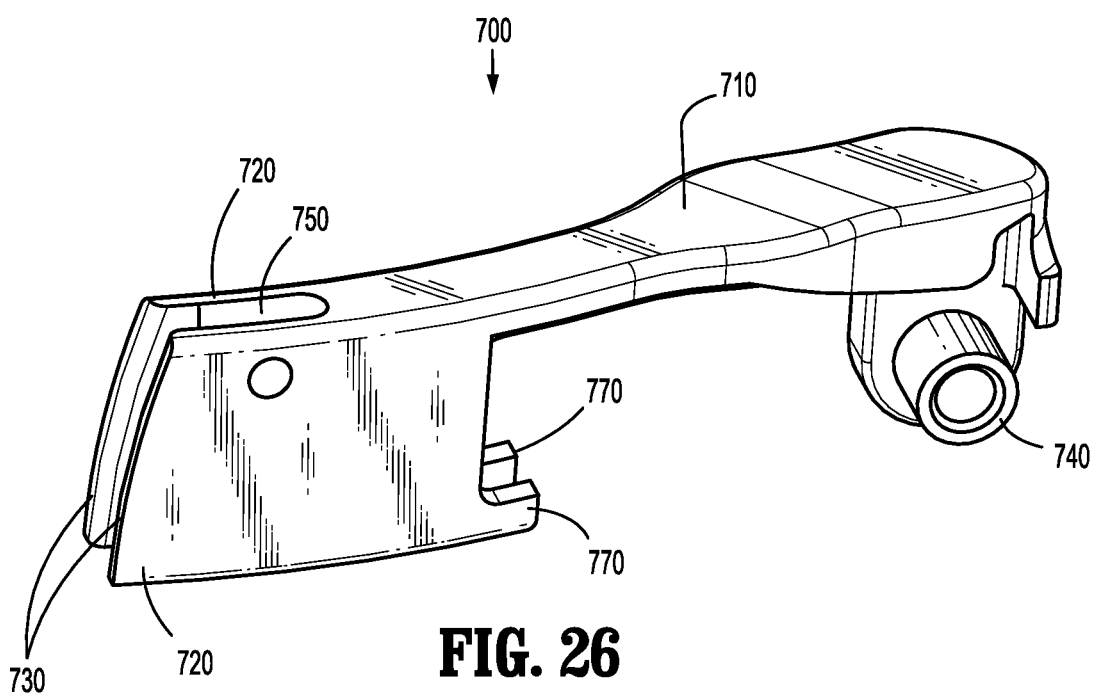
FIG. 26 is a perspective view of a tissue stop for use with the loading unit of FIGS. 3-10.

With reference to FIGS. 21 and 22, pushers 532 of the illustrated embodiments each engage two or more staples 530. Pushers 532 include a single distally-located triple pusher 532a (FIG. 23), a single proximally-located double pusher 532b (FIG. 24), and a series of triple pushers 532c (one triple pusher 532c is shown in FIG. 25) which extend between double pusher 532b and triple pusher 532a on each side of channel 526. In disclosed embodiments, portions of pushers 532a, 532b, 532c include various radii of curvature included therewith and are in the range of approximately 1.00 inches to about 1.50 inches. It is also disclosed that at least one pusher 532a, 532b, 532c includes no curved surfaces—only linearly angled surfaces.

Figure 2:
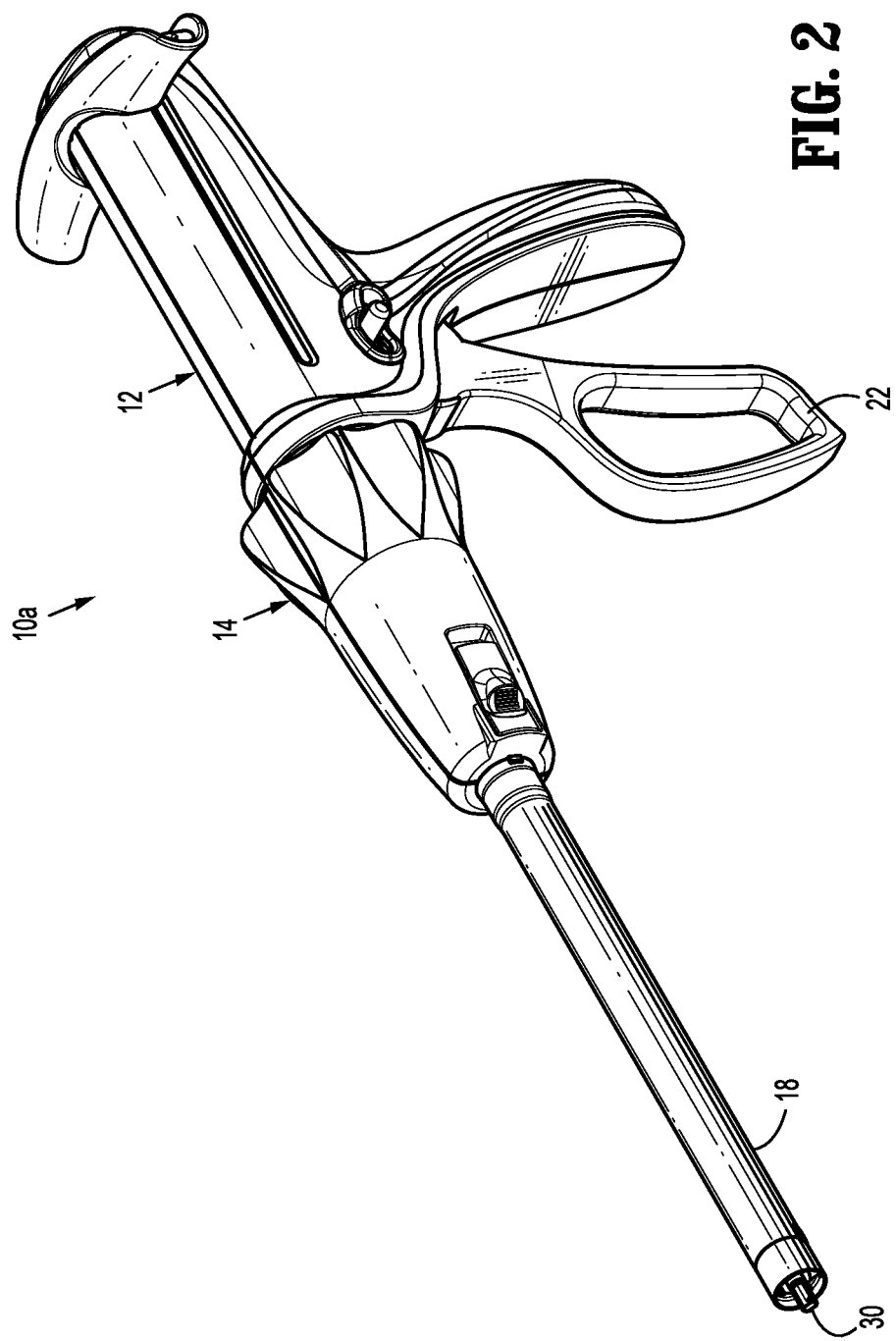
FIG. 2 is a perspective view of a handle assembly of the surgical stapling instrument of FIG. 1A.

During operation of stapler 10, actuation of its movable handle 22 through successive strokes causes distal advancement of its drive bar 30 (a distal portion of which is illustrated in FIG. 2), such that drive bar 30 pushes a drive assembly 560 through cartridge 518. (Further details of how actuation of movable handle 22 causes distal advancement of drive bar 30 are explained in U.S. Pat. No. 6,953,139 to Milliman et al., which has been incorporated by reference herein.) The movement of drive assembly 560, and in particular, a dynamic clamping member 606 affixed thereto, moves a longitudinally curved actuation sled 536 (see FIGS. 18-20) through cartridge 518. As sled 536 moves through cartridge 518, longitudinally curved cam wedges 534 of actuation sled 536 sequentially engage pushers 532 to move pushers 532 vertically within staple retention slots 528 and eject staples 530 into staple forming depressions 514 of anvil plate 512. Subsequent to the ejection of staples 530 from retention slots 528 (and into tissue), a cutting edge 606d of dynamic clamping member 606 severs the stapled tissue as cutting edge 606d travels through curved slot 526 of cartridge 518.

Referring to FIG. 8 and in accordance with embodiments of the present disclosure, cartridge 518 includes a tissue contacting surface 540 including surfaces 540a, 540b, and 540c. Surface 540a is adjacent longitudinal slot 526 and defines a first gap between tissue contacting surface 540 and a bottom surface 544 of anvil plate 512. Surface 540b is located adjacent surface 540a and defines a second gap between tissue contacting surface 540 and bottom surface 544. Surface 540c is located proximal to an outer perimeter of cartridge 518 and defines a third gap between tissue contacting surface 540 and bottom surface 544. The first gap is less than the second gap, which is less than the third gap. When anvil 506 is approximated towards cartridge 508, layers of tissue located between bottom surface 544 and tissue contacting surface 540 are compressed. Since the first gap is the smallest, tissue located between surface 540a and bottom surface 544 is compressed the most. Similarly, the tissue located between surface 540c and bottom surface 544 is compressed the least, with the tissue located between surface 540b and bottom surface 544 being compressed to an intermediate degree. The arrangement of surfaces 540a, 540b, 540c on tissue contacting surface 540 provides a tissue compression gradient extending transverse to a longitudinal axis of the cartridge 518.

Referring to FIGS. 8, 21 and 22 in conjunction with the stepped arrangement of tissue contacting surface 540, the illustrated embodiment of staples 530 include varying leg lengths for cooperating with the varying gaps. Staples 530a have the shortest leg length and are associated with surface 540a. Similarly, staples 530b have an intermediate leg length and are associated with surface 540b, while staples 530c have the longest leg length and are associated with surface 540c. The leg length of staples 530b is between the leg length of staples 530a and 530c. Since the tissue between surface 540a and bottom surface 544 has been compressed the most, the resulting thickness of the tissue is at a minimum, thereby allowing a staple having a shorter leg length (i.e. staple 530a) to be used to join the layers of tissue. The layers of tissue between surface 540b and bottom surface 544 are compressed to an intermediate degree of compression and the resulting thickness of the tissue layers allows a staple having an intermediate leg length (i.e. staple 530b) to be used when joining the layers of tissue. The layers of tissue between surface 540c and bottom surface 544 are compressed the least amount and are thicker than the other layers requiring staples that have the longest leg length (i.e. staples 530c) for joining the layers of tissue.

In particular, the illustrated embodiment of pusher 532 includes plates 531a, 531b, 531c, which cooperate with staples 530a, 530b, 530c, respectively. Plate 531a has a height which is greater than the height of plate 531b. Additionally, the height of plate 531b is greater than the height of plate 531c. Pusher 532 further includes cam members 542 that are longitudinally staggered. As sled 536 translates distally through cartridge 518, cam wedges 534 engage cam members 542 of pusher 532, thereby urging pusher 532 in a direction transverse to the longitudinal axis of cartridge 518 and urging staples 530 towards staple forming depressions 514 of anvil plate 512. In particular, cam wedges 534 are longitudinally staggered such that when they engage staggered cam members 542, the resulting forces applied to move pusher 532 towards tissue contacting surface 540 are evenly applied.

With continued reference to FIGS. 21 and 22, staples 530a, 530b, 530c ride on pusher 532 (for illustrative purposes, pusher 532c from FIG. 25 is shown). Additionally, cam members 542 of each pusher 532 include cam surfaces 542a and 542b. Each cam surface 542a, 542b is configured to be contacted by cam wedges 534. In particular, and with reference to FIGS. 21-25, cam wedges 534a are configured to cam surfaces 542a; cam wedges 534b are configured to engage cam surfaces 542b; central section 534c of sled 536 is configured to travel through slot 526.

Referring to FIG. 20, the illustrated embodiment of actuation sled 536 includes a longitudinally curved projection 535 depending from a lower surface thereof. Projection 535 is configured to travel within a slot 515 (FIG. 10) of channel or carrier 516. In disclosed embodiments, the radius of curvature of both cam wedges 534 and projection 535 is between about 1.00 inches and about 2.00 inches, and in particular, may be approximately 1.40 inches.

With reference to FIG. 10, proximal body portion 502 includes an inner body 503 formed from molded half-sections 503a and 503b, a drive assembly 560 and a drive locking assembly 564. Proximal body portion 502 is coupled to tool assembly 504 by a mounting assembly 570. Mounting assembly 570 has a pair of extensions 576 which extend into a proximal end of carrier 516. Each extension 576 has a transverse bore 578 which is aligned with a hole 580 in the cartridge 518 such that mounting assembly 570 is pivotally secured to cartridge 518 by pin 582. Mounting assembly 570 is fixedly secured to half-section 503a by a pair of vertical protrusions 584. Vertical protrusions 584 extend upwardly from mounting assembly 570 and frictionally fit into corresponding recesses (not shown) in half-section 503a.

With continued reference to FIG. 10, the illustrated embodiment of anvil cover 510 includes a proximally extending finger 588 having a pair of cutouts 590 formed therein. Cutouts 590 are positioned on each lateral side of finger 588 to help secure anvil cover 510 to half-section 503a. More particularly, half-section 503a includes a channel 505 therein, and channel 505 includes a pair of protrusions 505a. Finger 588 of anvil cover 510 mechanically engages channel 505 of half-section 503a, such that cutouts 590 are aligned with protrusions 505a. An outer sleeve 602 covers the finger and channel. The configuration of finger 588 and channel 505 facilitates a secure connection between anvil cover 510 and half-section 503a. Moreover, this connection results in a non-movable (e.g., non-pivotable) anvil assembly 506 with respect to proximal body portion 502.

Figure 11:
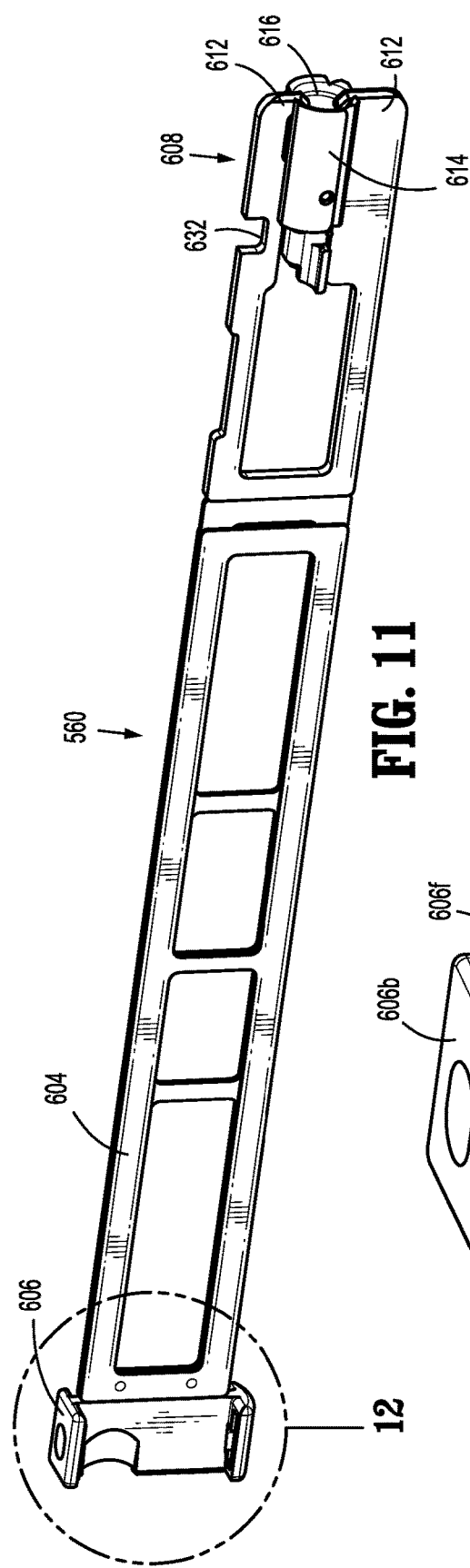
FIG. 11 is a perspective view of a drive assembly and dynamic clamping member of the loading unit of FIGS. 3-10.
Figure 12:
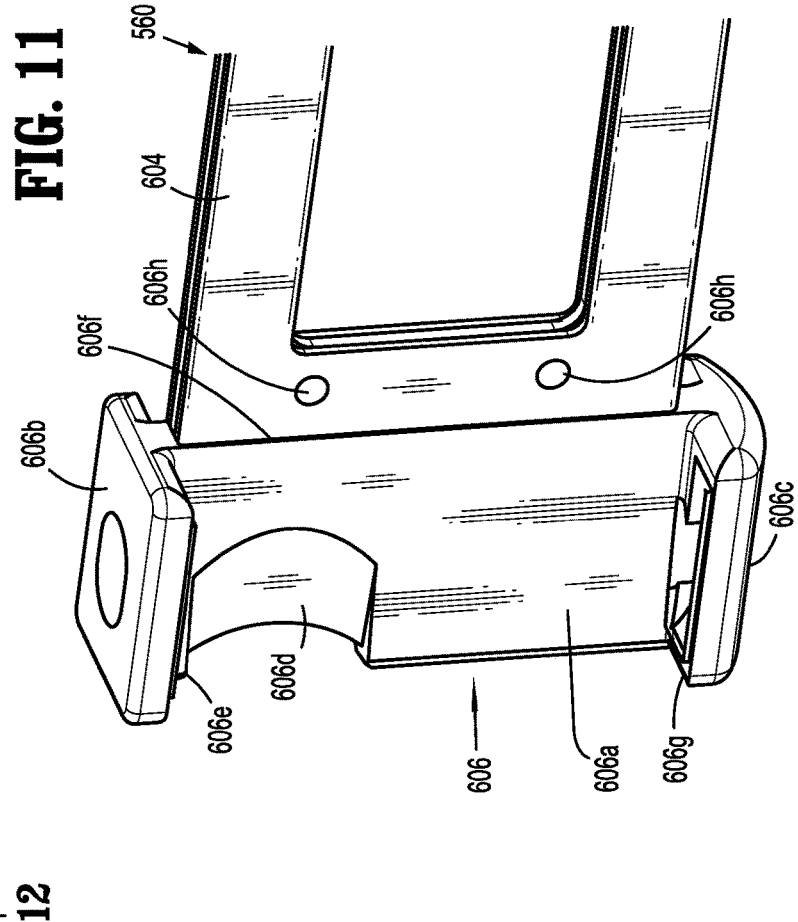
FIG. 12 is an enlarged view of the area of detail of FIG. 11.
Figure 13:
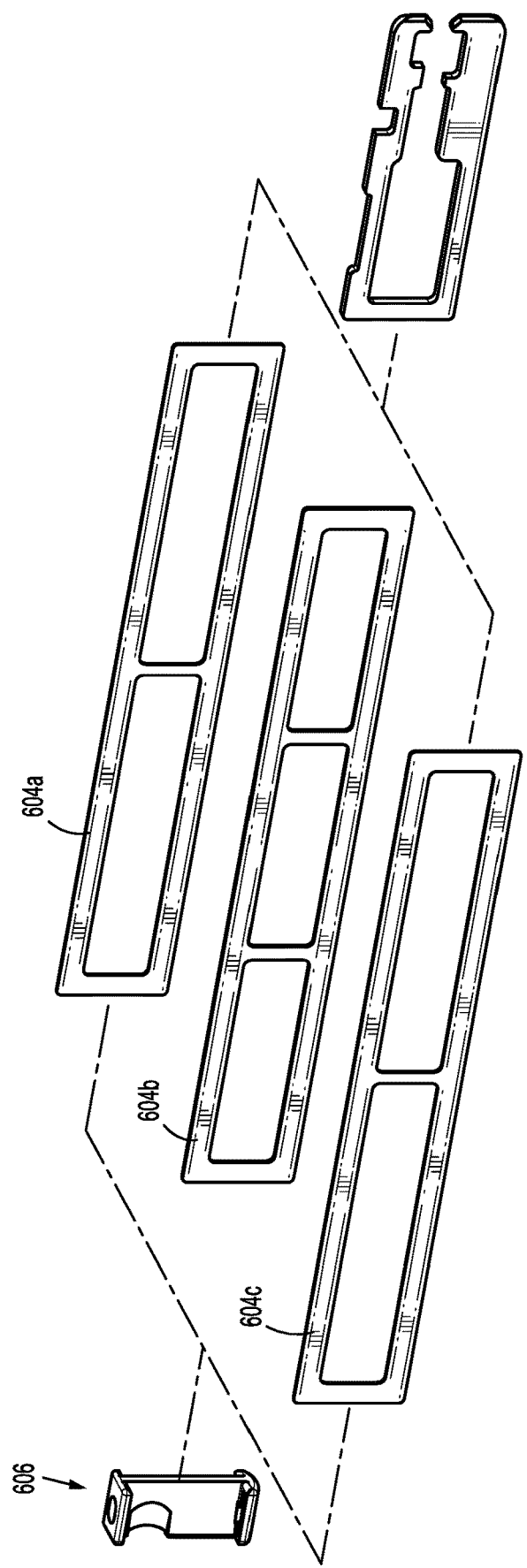
FIG. 13 is a perspective assembly view of the drive assembly and dynamic clamping member of FIGS. 11 and 12.
Figure 14:
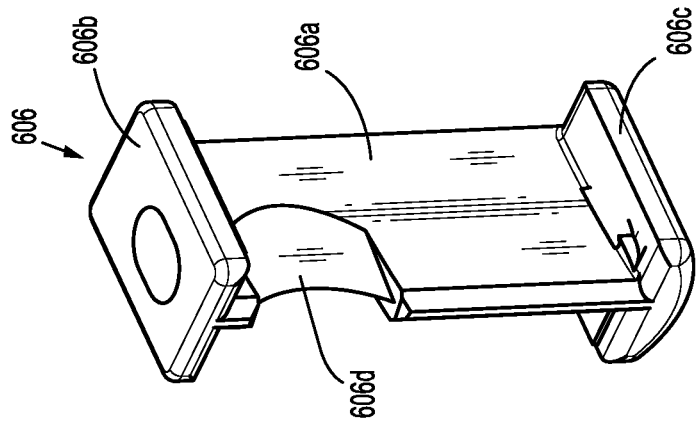
FIGS. 14-17 are various views of the dynamic clamping member according to an embodiment of the present disclosure.

Referring to FIGS. 11-13, drive assembly 560 includes a flexible drive beam 604 which is constructed from three stacked metallic sheets 604a-c and a proximal engagement portion 608. At least a portion of drive beam 604 is sufficiently flexible to be advanced through the curvature of the tool assembly 504. Drive beam 604 has a distal end which is secured to a dynamic clamping member 606 via a butt weld 606f (FIG. 12). Spot welds 606h, which are configured to hold sheets 604a-c together, are also shown in FIG. 12.

Engagement section 608 is fastened to a proximal portion of middle sheet 604b (e.g., via a butt weld) and includes a stepped portion defining a shoulder 610. A proximal end of engagement section 608 includes diametrically opposed inwardly extending fingers 612. Fingers 612 engage a hollow drive member 614 to fixedly secure drive member 614 to the proximal end of beam 604. Drive member 614 defines a proximal porthole 616 which receives the distal end of a control rod of drive bar 30 (see FIG. 2) when loading unit 500 is attached to surgical stapling instrument 10.

Figure 16:
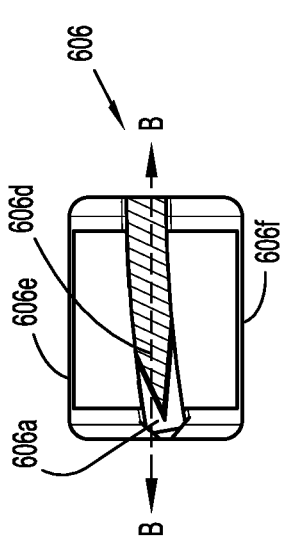
Figure 15:
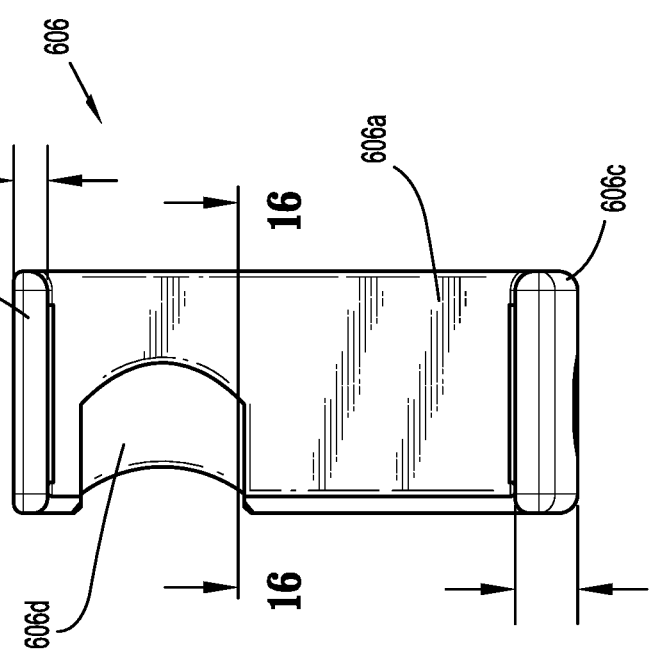

With reference to FIGS. 14-17, dynamic clamping member 606 includes a vertical strut 606a, an upper beam 606b and a lower beam 606c. A knife or cutting edge 606d is formed on a distal face of vertical strut 606a. As illustrated, the width of vertical strut 606a is equal to the width of drive beam 604 of drive assembly 560 (see FIG. 12). With particular reference to FIG. 16, vertical strut 606a and knife 606d are longitudinally curved from a first lateral side 606e of clamping member towards a second lateral side 606f of clamping member 606. Both upper beam 606b and lower beam 606c are linearly disposed with respect to longitudinal axis "A-A."

As illustrated in FIGS. 14-17A, the present disclosure includes embodiments of dynamic clamping member 606 that are asymmetrical. For instance, in the embodiment illustrated in FIGS. 15 and 17, lower beam 606c is thicker than upper beam 606b. In this embodiment, dynamic clamping member 606 is asymmetrical about horizontal axis "H-H" illustrated in FIG. 17. It is envisioned that lower beam 606c includes a thickness "$T_L$", which is between about 0.050 inches and about 0.100 inches, and in particular, may be approximately 0.068 inches. It is envisioned that upper beam 606b includes a thickness "$T_U$", which is between about 0.025 inches and about 0.050 inches, and in particular, is approximately 0.037 inches.

Figure 17:
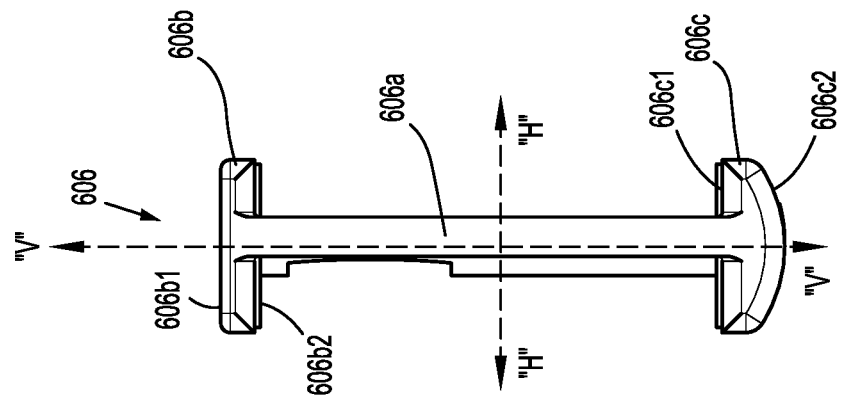

An additional example of an asymmetrical dynamic clamping member 606 is also illustrated in FIG. 17. In this embodiment, the transverse cross-sectional shape of upper beam 606b includes an upper planar surface 606b1 and a lower planar surface 606b2. The cross-sectional shape of lower beam 606c includes an upper planar surface 606c1 and a lower arcuate surface 606c2. In this embodiment, dynamic clamping member 606 is asymmetrical about the horizontal axis "H-H."

The embodiment shown in FIGS. 16 and 17 illustrates proximal portion of vertical strut 606a being off-center with respect to the remainder of clamping member 606. More particularly, it is envisioned that the center of vertical strut 606a is between about 0.070 inches and about 0.090 inches (e.g., approximately 0.080 inches) from first lateral side 606e of clamping member 606, and is between about 0.90 inches and about 0.110 inches (e.g., approximately 0.100 inches) from second lateral side 606f of clamping member 606. In this embodiment, dynamic clamping member 606 is asymmetrical about vertical axis "V-V" illustrated in FIG. 17.

Figure 17A:
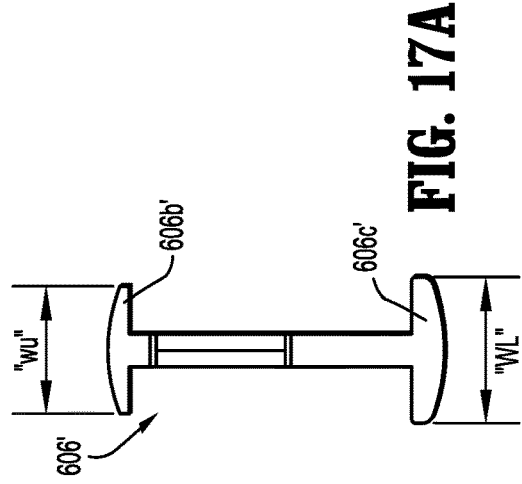
FIG. 17A is a rear view of another embodiment of a dynamic clamping member according to another embodiment of the present disclosure.

With reference to FIG. 17A, dynamic clamping member 606' is shown. Lower beam 606c' is wider than upper beam 606b' of dynamic clamping member 606'. More particularly, it is envisioned that a width "wl" of lower beam 606c' is between about 0.180 inches and about 0.200 inches, and that a width "wu" of upper beam 606b' is between about 0.160 inches and about 0.180 inches. In this embodiment, dynamic clamping member 606' is asymmetrical about the horizontal axis "H-H." Further, while not explicitly shown, it is envisioned that upper beam 606b' is wider than lower beam 606c' of a dynamic clamping member 606 of the present disclosure. Additionally, dynamic clamping member 606' is shown as being longitudinally linear (vis-à-vis longitudinally curved), in accordance with embodiments of the present disclosure.

The asymmetrical embodiments of dynamic clamping member 606 of the present disclosure help ensure proper orientation of dynamic clamping member 606 during assembly of surgical stapling instrument 10 or loading unit 500. That is, the asymmetry of dynamic clamping member 606 prevents dynamic clamping member 606 from improper placement with respect to tool assembly 504, since dynamic clamping member 606 can only physically fit in a particular orientation. In particular, the asymmetry ensures that knife 606d faces distally and is positioned to travel through the space between cartridge assembly 508 and anvil assembly 506, for example.

Figure 17B:
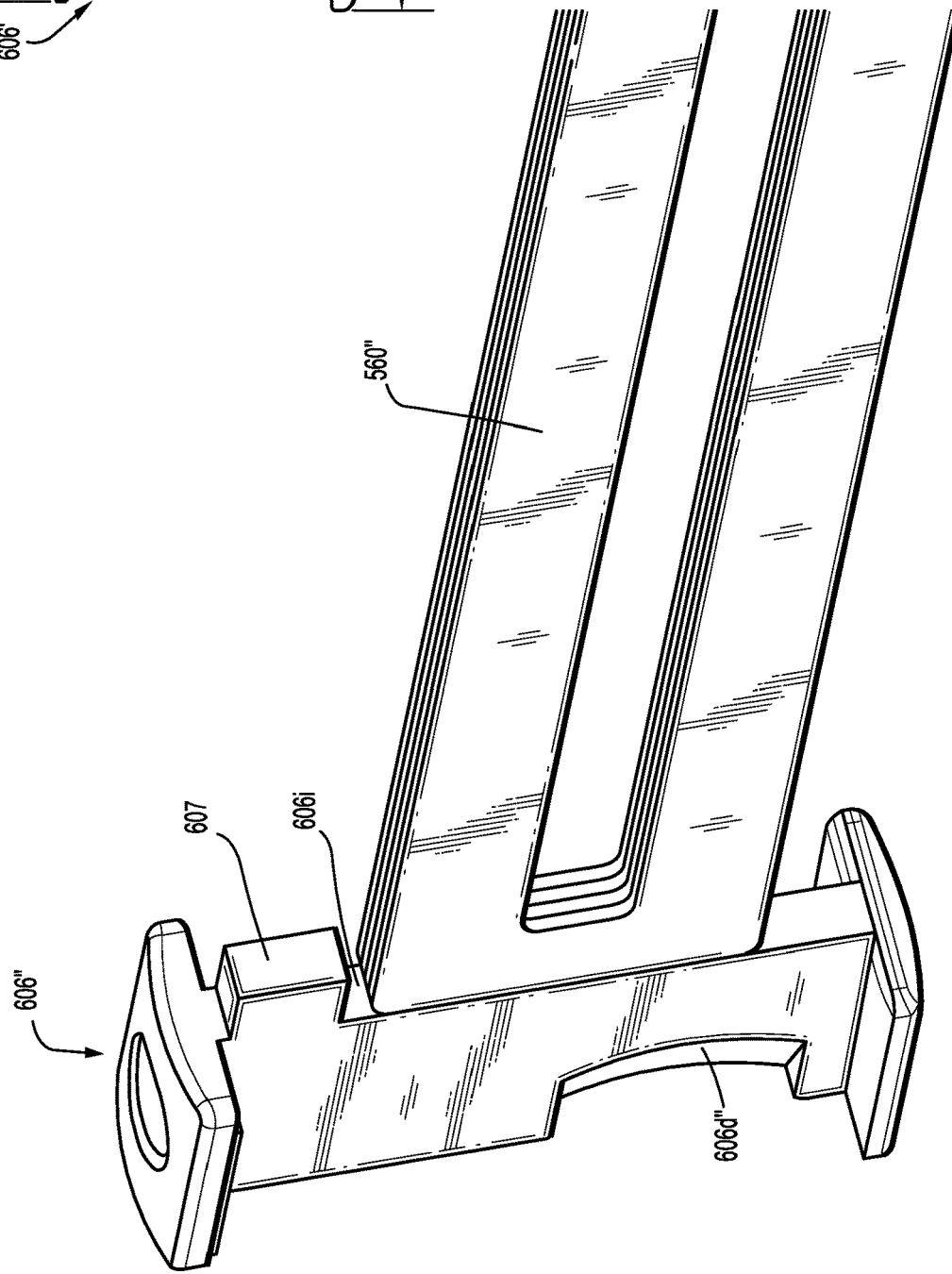
FIG. 17B is a perspective view of another embodiment of a dynamic clamping member according to another embodiment of the present disclosure.

With reference to FIG. 17B, the present disclosure includes another embodiment of a dynamic clamping member 606" that is also configured to help ensure proper orientation of dynamic clamping member 606" during assembly of surgical stapling instrument 10 or loading unit 500. Dynamic clamping member 606" includes a protrusion 607 extending from a proximal surface 606i thereof. In the illustrated embodiment, a drive assembly 560" has a smaller height than embodiment of drive assembly 560' illustrated in FIGS. 10-13. Protrusion 607 is shown being disposed on a lower portion of dynamic clamping member 606" (i.e., on the opposite side as cutting edge 606d") and to one side of drive assembly 560", but it is envisioned that protrusion 607 is disposed on the other side of drive assembly 560".

As discussed above, the inclusion of protrusion 607 helps ensure proper orientation of dynamic clamping member 606". More particularly, it is envisioned that extensions 576 of mounting assembly 570 would physically prevent further assembly of dynamic clamping member 606" being incorrectly fastened to drive assembly 560" (e.g., when dynamic clamping member 606" is up-side-down with respect to drive assembly 560".

It is further envisioned that dynamic clamping member 606, 606' may include any combination of the asymmetrical features discussed herein and may also include protrusion 607 of dynamic clamping member 606".

With additional reference to dynamic clamping member 606 of FIGS. 14-17A, it is envisioned that each of upper beam 606b and 606c includes a plastic material or layer which is injection molded onto an outwardly facing surface of each beam 606b and 606c. Plastic layer provides reduced frictional engagement between dynamic clamping member 606 and cartridge and anvil assemblies 508 and 506, respectively, during actuation of tool assembly 504.

Referring back to FIG. 8, channel 511 is configured and dimensioned accordingly to accommodate a corresponding embodiment of upper beam 606b of clamping member 606; slot 526 is configured and dimensioned accordingly to accommodate a corresponding embodiment of vertical strut 606a of clamping member 606. As can be appreciated, when used with the embodiment of dynamic clamping member 606 of FIG. 17A, channel 511 is too narrow to accommodate lower beam 606c of dynamic clamping member 606.

With reference to FIG. 10, when drive assembly 560 is advanced distally within tool assembly 504, upper beam 606b moves within channel 511 defined between anvil plate 512 and anvil cover 510, and lower beam 606c moves over an exterior surface of carrier 516. When lower beam 606c engages and moves over cam surface 516a, cartridge assembly 508 pivots from the open position to the closed position. As dynamic clamping member 606 continues to move distally along and through tool assembly 504, the maximum gap between anvil plate 512 and cartridge 518 is defined by engagement of layer 606e on upper beam 606b (FIG. 12) and a lower surface defining channel 511, and engagement of a layer 606g on lower beam 606c with the external surface of carrier 516. In disclosed embodiments, the height of channel 511 is greater than the height of upper beam 606b, providing clearance between the upper surface of dynamic clamping member 606 and the anvil plate 512 so that upper beam 606b of dynamic clamping member 600 does not simultaneously engage the upper and lower surfaces of anvil channel 511.

With continued reference to FIG. 10, loading unit 500 includes a locking mechanism 564 including a locking member 620 and a locking member actuator 622. Locking member 620 is rotatably supported within a longitudinal or axial slot 625 formed in a proximal portion of an upper housing half 503a of inner body 503 of loading unit 500. Locking member 620 is movable from a first position, in which locking member 620 maintains drive assembly 560 in a prefired position, to a second position in which drive assembly 560 is free to move axially.

Locking member 620 includes a semi-cylindrical body 624 which is slidably positioned within transverse slot 625 formed in upper housing half 503a of body portion 503. Body 624 includes a radially inwardly extending cam member 628 and a radially inwardly extending finger 630. Finger 630 is dimensioned to be received within a notch 632 formed in drive assembly 560. Engagement of finger 630 in notch 632 of drive assembly 560 prevents drive assembly 560 from moving linearly within body portion 503 to prevent actuation of loading unit 500 prior to attachment of loading unit 500 to surgical instrument 10.

Locking member actuator 622 is slidably positioned within axial slot 625 formed in upper housing half section 503a of body portion 503 of loading unit 500. Actuator 622 includes a proximal abutment member 636, a distal spring guide 627, and a central cam slot 640. Axial slot 641 in the housing half section 503a intersects transverse slot 625 such that cam member 628 of locking member 620 is slidably positioned within cam slot 640 of locking member actuator 622. A biasing member or spring 642 is positioned about spring guide 627 between a distal surface of actuator 622 and a wall 641a defining the distal end of axial slot 641. Spring 642 urges actuator 622 to a first position within axial slot 641. In the first position, abutment member 636 is positioned on insertion tip 650 of proximal body portion 502 (FIG. 3) and cam slot 640 is positioned to locate cam member 628 such that finger 630 of lock member 620 is positioned within notch 632 of drive assembly 560.

Prior to attachment of loading unit 500 onto surgical instrument 10, spring 642 urges actuator 622 to the first position to maintain the lock member 620 in its first position as discussed above. When insertion tip 650 of loading unit 500 is linearly inserted into the open end of the body portion 18 (FIG. 2) of surgical instrument 10, nubs 652 of insertion tip 650 (FIG. 3) move linearly through slots (not shown) formed in open end of body portion 18. As nubs 652 pass through the slots, the proximal end of abutment member 636, which is angularly offset from nubs 652, abuts a wall defining the slots for receiving nubs. As loading unit 500 is moved farther into body portion, locking member actuator 622 is moved from its first position to its second position. As actuator 622 is moved to its second position, lock member 620 is cammed from its first position engaged with notch 632 of drive assembly 560 to its second position to move finger 630 from notch 632. The locking mechanism including locking member 620 and locking member actuator 622 prevents advancement of the drive assembly 560 of loading unit 500 prior to loading of loading unit 500 onto a surgical instrument 10.

Figure 3:
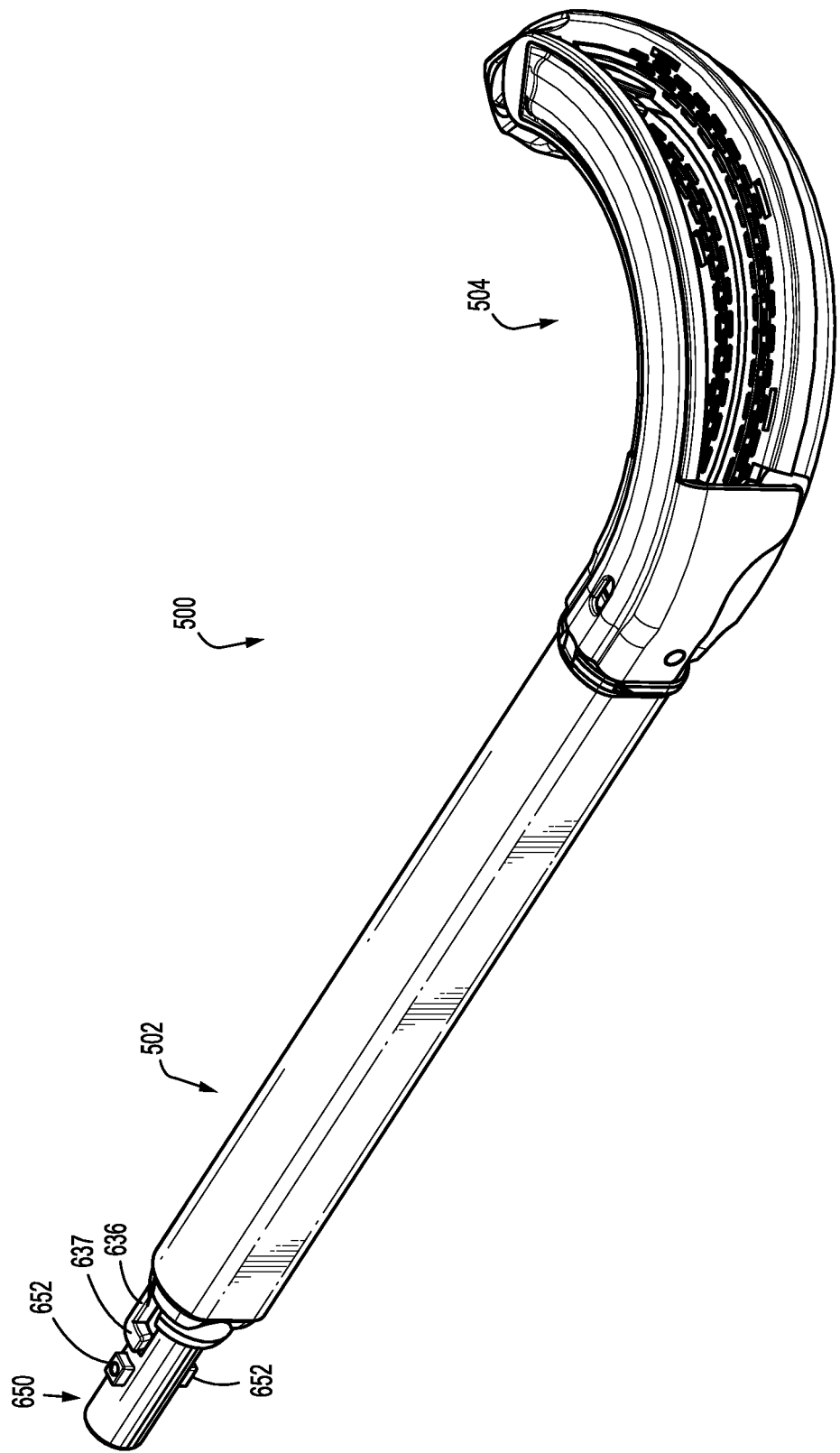
FIG. 3 is a perspective view of the loading unit of FIGS. 1 and 1A.

In the embodiments illustrated in FIGS. 3 and 10, locking member actuator 622 includes an articulation lock portion 637 disposed thereon. In particular, articulation lock portion 637 extends in an approximate right angle from abutment member 636. Articulation lock portion 637 is configured to physically prevent the longitudinal translation of an articulation member (not shown) of a handle portion of a surgical instrument having articulation capabilities. That is, even when loading unit 500 is engaged with a surgical instrument 10 that is otherwise capable of articulation (i.e., pivotable movement of the jaw members with respect to the elongated portion 18), articulation lock portion 637 of loading unit 500 prevents an articulation member from entering loading unit 500.

Referring to FIG. 10, upper half-section 503a of proximal body portion 502 defines a longitudinal slot 660 which receives a leaf spring 662. Leaf spring 662 is confined within slot 660 by outer sleeve 602. Leaf spring 662 has an angled proximal end 664 which is positioned to abut shoulder 610 (FIG. 11) of engagement section 608 of drive beam 604 when drive beam 604 is in its retracted position. When drive beam 604 is advanced distally by advancing drive bar 30, as described above, leaf spring 662 is flexed upwardly by shoulder 610 of drive beam 604 to permit distal movement of drive beam 604.

Referring to FIGS. 4, 7, and 26-30, loading unit 500 also includes a tissue stop 700. Tissue stop 700 includes a body 710, a pair of legs 720 extending proximally from the body 710, a stopping portion 730, a pair of laterally opposed protrusions 740 extending transversely from body 710 (See FIG. 26), and a knife channel 750 disposed between pair of legs 720. Tissue stop 700 is pivotally connected to a distal portion of cartridge assembly 508 via the engagement between protrusions 740 and a corresponding pair of apertures (not shown) disposed within cartridge assembly 508. Cartridge assembly 508 includes an opening 519 (FIGS. 7 and 10) adapted to receive both legs 720 of tissue stop 700. A recess 521 is positioned distally of opening 519 and is adapted to receive a portion of tissue stop 700 therein. The recess 521 and opening 519 are shown in FIG. 10.

Figure 4:
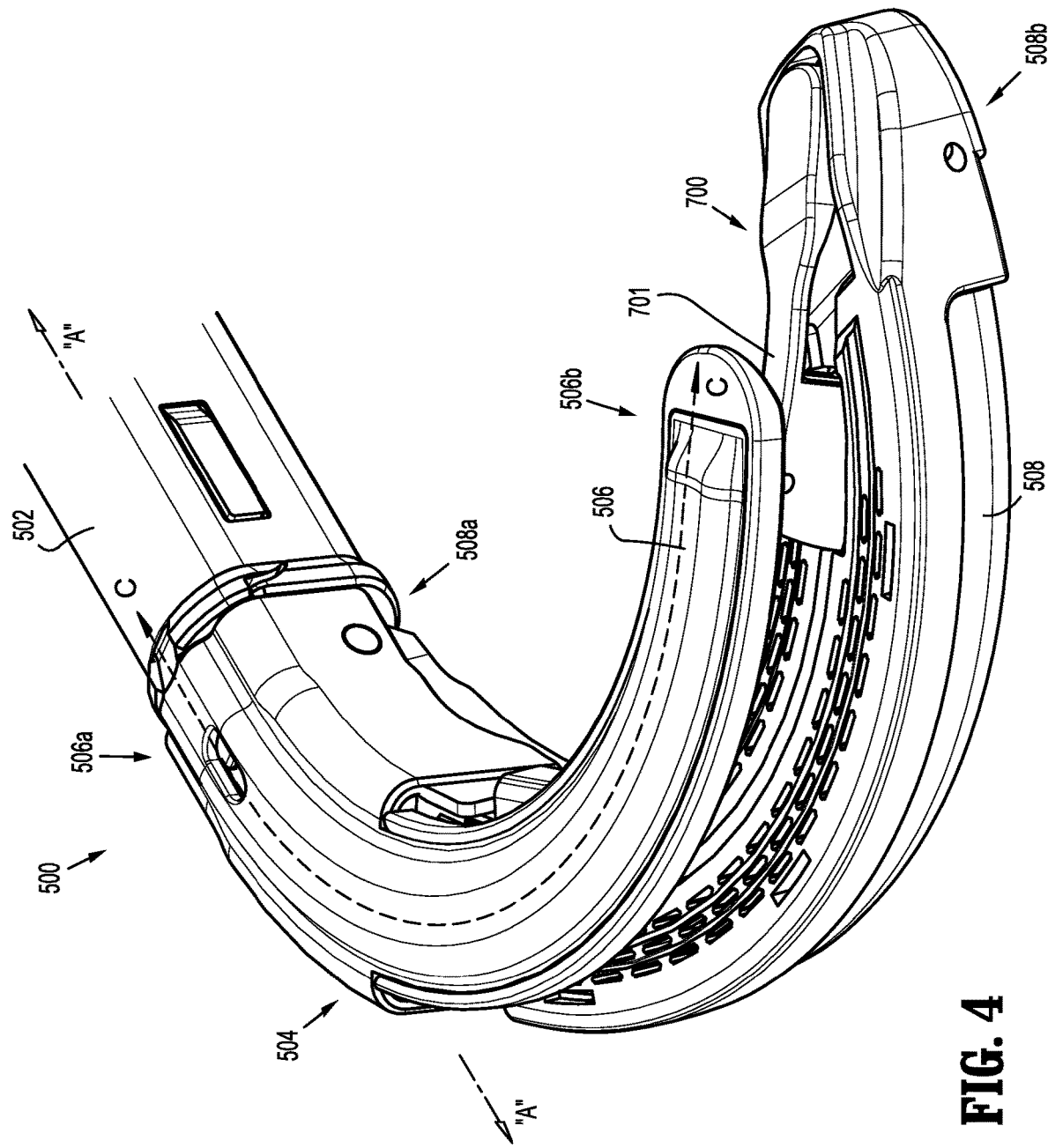
FIG. 4 is an enlarged view of the area of detail of FIGS. 1 and 1A.

Tissue stop 700 is movable between a first position (FIG. 4), which corresponds to when the jaw members are in an open position where an upper surface 701 thereof is disposed between cartridge assembly 508 and anvil assembly 506 (FIG. 4 illustrates the jaw members in a partially approximated position; FIG. 6 illustrates the jaw members in a fully opened position), and a second position (FIG. 30), which corresponds to when the jaw members are in the approximated position and where upper surface 701 of tissue stop 700 is substantially flush with tissue contacting surface 514 of cartridge 518. (In FIG. 30, upper surface 701 is hidden as upper surface 701 is within cartridge assembly 508.) A biasing member 760 (FIG. 10), a portion of which is disposed around protrusion 740, urges tissue stop 700 towards its first position. Tissue stop 700 also includes a finger 770 (FIG. 26) extending distally from each leg 720. With specific reference to FIG. 27, when the jaw members are in the open position, fingers 770 of tissue stop 700 engage a lip 523 disposed on cartridge assembly 508 to limit the amount of movement imparted by biasing member 760 in the general direction of arrow "B" in FIG. 27.

Figure 28:
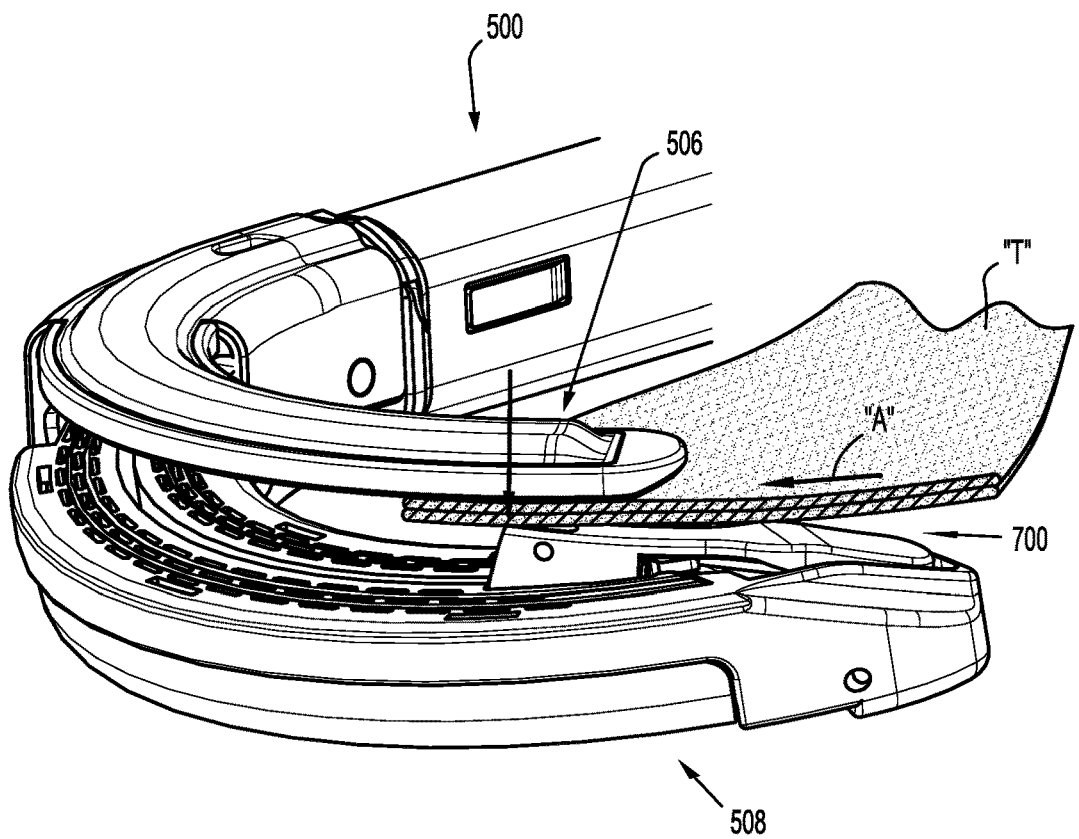
FIGS. 28-30 are perspective views of the loading unit of FIGS. 3-10 interacting with a layer of tissue at various stages of operation of the loading unit.
Figure 29:
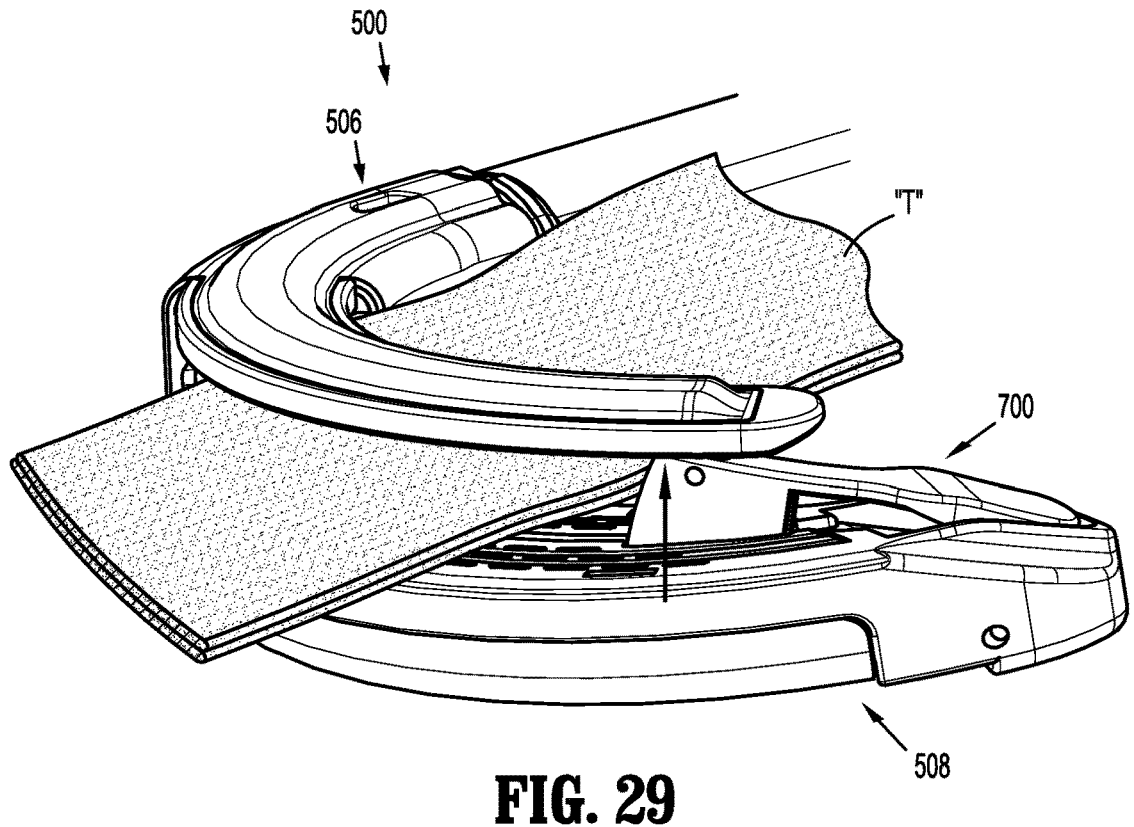
Figure 30:
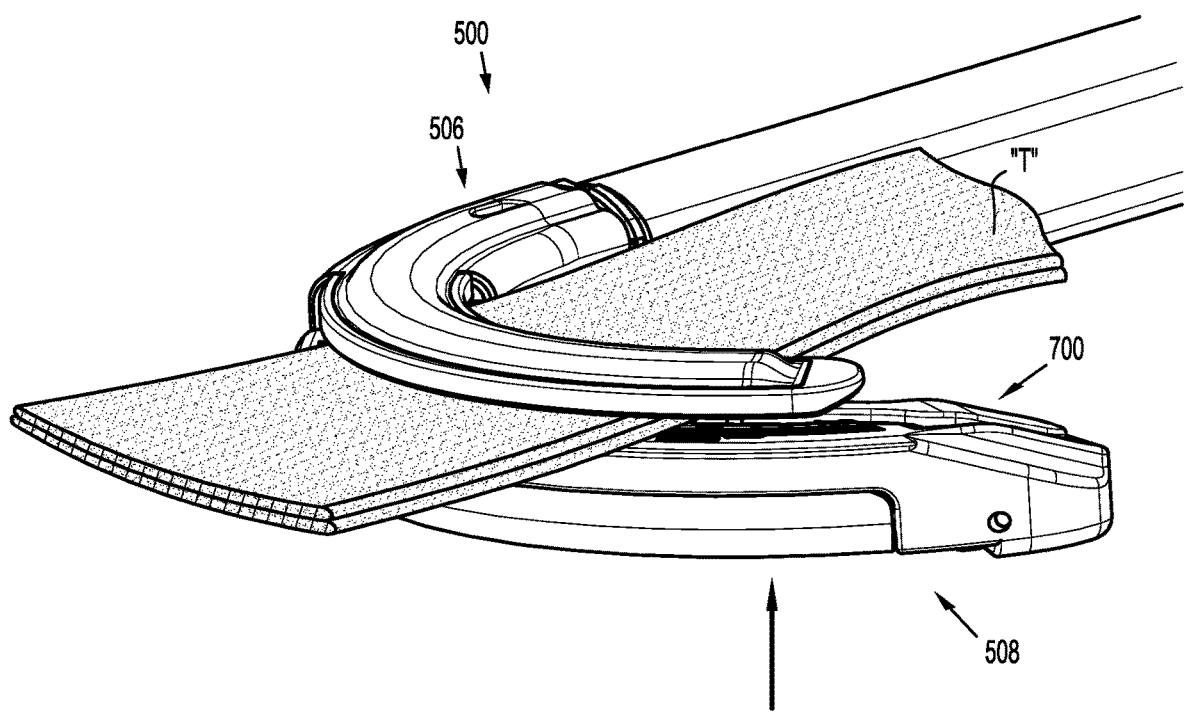

When tissue stop 700 is in its first position, tissue "T" is proximally insertable (in the general direction of arrow "A" in FIG. 28) from distally beyond tissue stop 700, to a location that is between anvil assembly 206 and cartridge assembly 508 and proximal of tissue stop 700 (see FIGS. 28 and 29). In this position, stopping portion 730, which is disposed at an oblique angle (e.g., between about 45° and about 90°) with respect to tissue contacting 540 of cartridge assembly 508, impedes tissue from distally escaping the tool assembly 504. When the jaw members are approximated (e.g., when cartridge assembly 508 is pivoted towards anvil assembly 506), tissue stop 700 (or tissue "T") contacts anvil assembly 506, thus causing tissue stop 700 to pivot from its first position towards its second position. Legs 720 of tissue stop 700 are configured to lie within opening 519 (i.e., equal to or below the tissue contacting surface 540) of cartridge assembly 508 when tissue stop 700 is in its second position, such that legs 720 do not interfere with the location of the tissue with respect to the cartridge assembly 508 and respect to anvil assembly 506 (i.e., so that the staples can be deployed into tissue lying over the tissue stop). When the cartridge assembly 508 moves away from anvil assembly 506, tissue stop 700, under the influence of biasing member 760, returns to its first position.

With additional regard to knife channel 750, knife channel 750 is configured to allow vertical strut 606a (including cutting edge 606d) of dynamic clamping member 606 to travel distally past a portion of tissue stop 700 (i.e., at least to a location adjacent the distal-most longitudinal slot 528). Additionally, it is envisioned that at least a portion of knife channel 750 (e.g., the portion that is contacted by cutting edge 606d) is over molded with plastic or another suitable material.

While not explicitly illustrated, it is also envisioned that tissue stop 700 is usable with a surgical instrument having parallel jaws and/or an electrosurgical instrument. An example of a surgical instrument having parallel jaws is described in commonly-owned U.S. Pat. No. 7,237,708 to Guy et al., the entire contents of which are hereby incorporated by reference herein. An example of an electrosurgical instrument is described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

The present disclosure also relates methods of using the described surgical instrument 10 or loading unit 500 to perform a lower anterior resection. Such a method includes providing surgical instrument 10 or loading unit 500, positioning jaw members adjacent tissue, approximating one jaw member (e.g., cartridge assembly 508) with respect to the other jaw member (e.g., anvil assembly 506), advancing drive assembly 560 such that dynamic clamping member 606 and at least a portion of drive assembly 560 move along a curvilinear path to cause staples 530 to be ejected into tissue "T" and to cut tissue "T." In certain embodiments, the jaw members are approximated, and the interior of the intestinal tissue is then washed out or otherwise cleansed. The tissue is then cut and stapled. In this way, the interior intestinal tissue is cleansed up to the location of the jaw members.

The present disclosure also relates to methods of assembling surgical instrument 10 or loading unit 500. Such a method includes positioning asymmetrical dynamic clamping member 606, 606' in mechanical engagement with a portion of tool assembly 504, and wherein the positioning step automatically results in the proper positioning of asymmetrical dynamic clamping member 606. Another method includes attaching dynamic clamping member 606" to drive assembly 560" in a way that would enable fail-safe positioning of dynamic clamping member 606" with respect to tool assembly 504.

Figure 31:
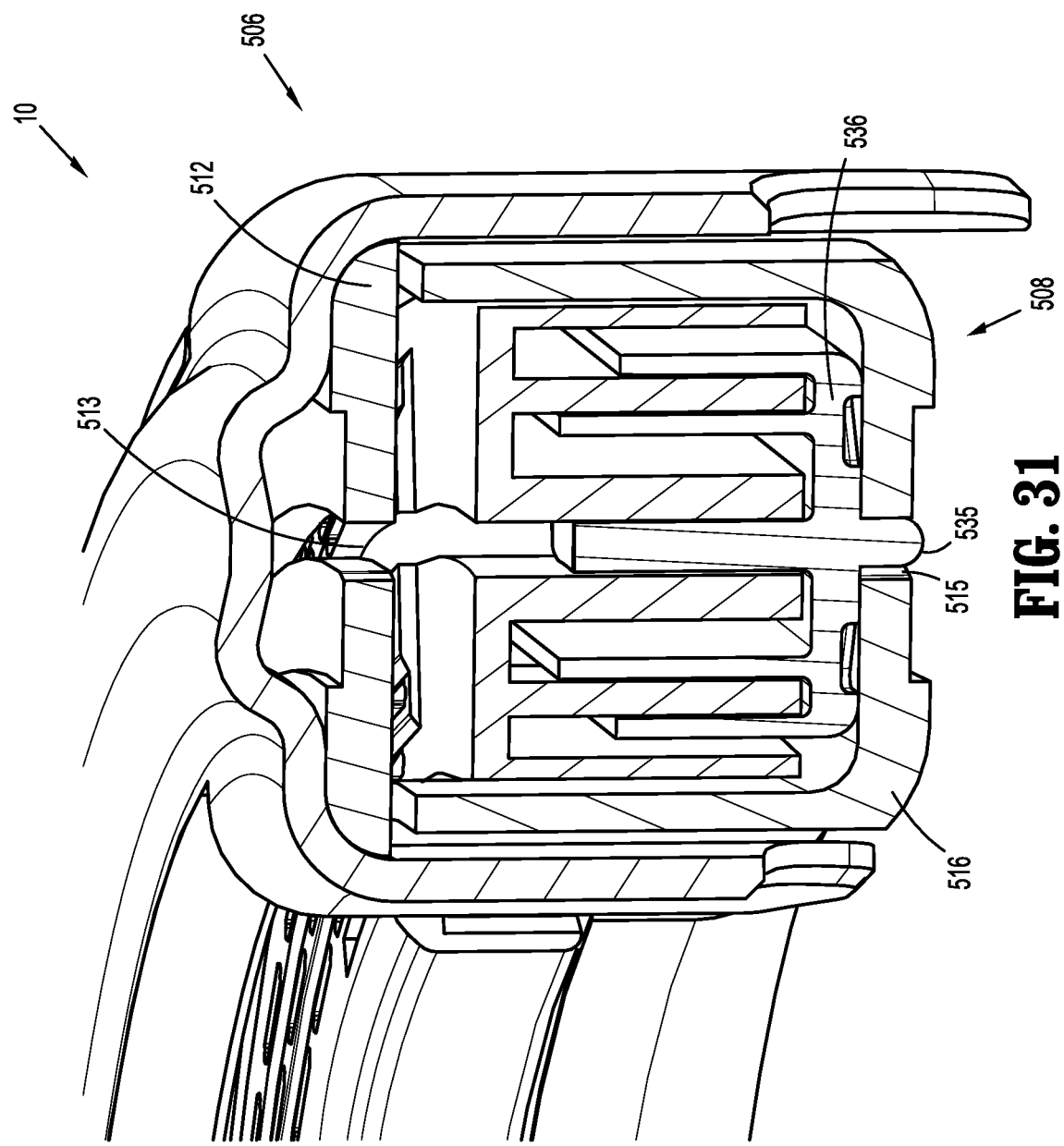
FIG. 31 is a transverse cross-sectional view of the surgical instrument taken across a portion of the actuation sled in accordance with an embodiment of the present disclosure.
Figure 32:
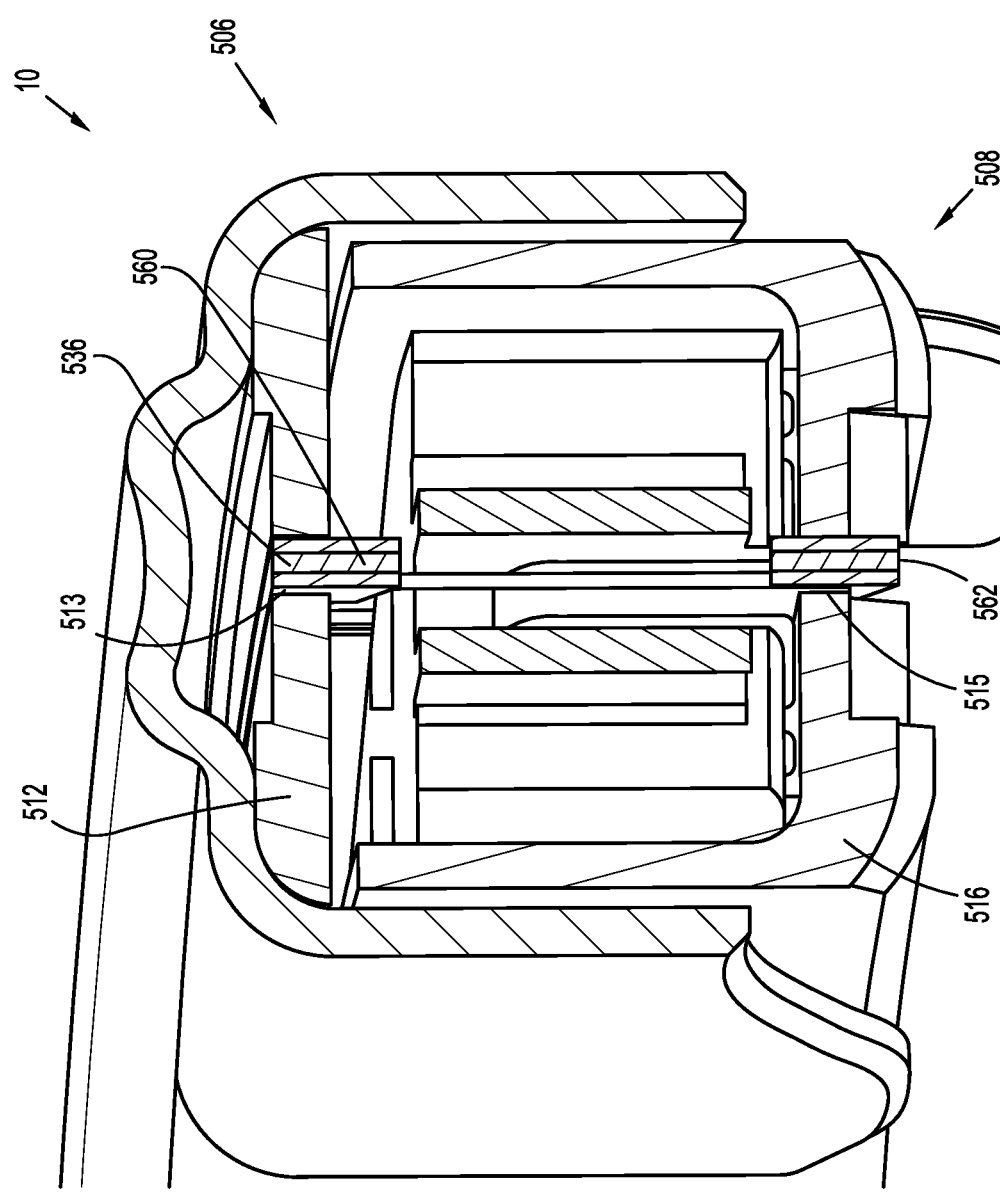
FIG. 32 is a transverse cross-sectional view of the surgical instrument of FIG. 30 taken across a portion of the drive assembly.

Other features of the present disclosure are shown in the cross-sectional views of FIGS. 31-32. Surgical instrument 10 includes the actuation sled 536 (FIG. 31) and drive assembly 560 (FIG. 32).

With particular reference to FIG. 31, a transverse cross-sectional view of surgical instrument 10 (e.g., loading unit) taken along a portion of actuation sled 536 is shown. The jaw members of surgical instrument 10 are shown and include an anvil assembly 506 and a cartridge assembly 508, which includes a channel or carrier 516. Here, actuation sled 536 includes a projection 535 depending from a lower surface thereof. (FIG. 20 also illustrates actuation sled 536 having projection 535 depending from a lower surface thereof.) Projection 535 is configured to travel within a slot 515 of a carrier 516. As actuation sled 536 is translated distally, projection 535 helps ensure that actuation sled 536 follows the curvature of the jaw members.

With particular reference to FIG. 32, a transverse cross-sectional view of surgical instrument 10 taken along a portion of drive assembly 560 is shown. Here, drive assembly 560 includes a lower portion 562 that is configured to travel within slot 515 of carrier 516. Additionally, an upper portion 563 of drive assembly 560 is configured to travel with a slot 513 (see also FIG. 31, for example) in anvil plate 512. For example, the drive beam 604 extends into the slot 515 and may also extend into slot 513. Upon distal translation of drive assembly 560, the interaction between lower portion 562 and upper portion 563 of drive assembly 560 with slots 515 and 513, respectively, helps ensure that drive assembly 560 follows the curvature of the jaw members. It is also envisioned and within the scope of the present disclosure that drive assembly 560 only engages a single slot 513 or 515. As noted above, these structures can be incorporated in a surgical instrument that does not have a loading unit incorporating the jaws of the instrument in a replaceable assembly and in which the staple cartridge is removable and/or reloadable.

Figure 33:
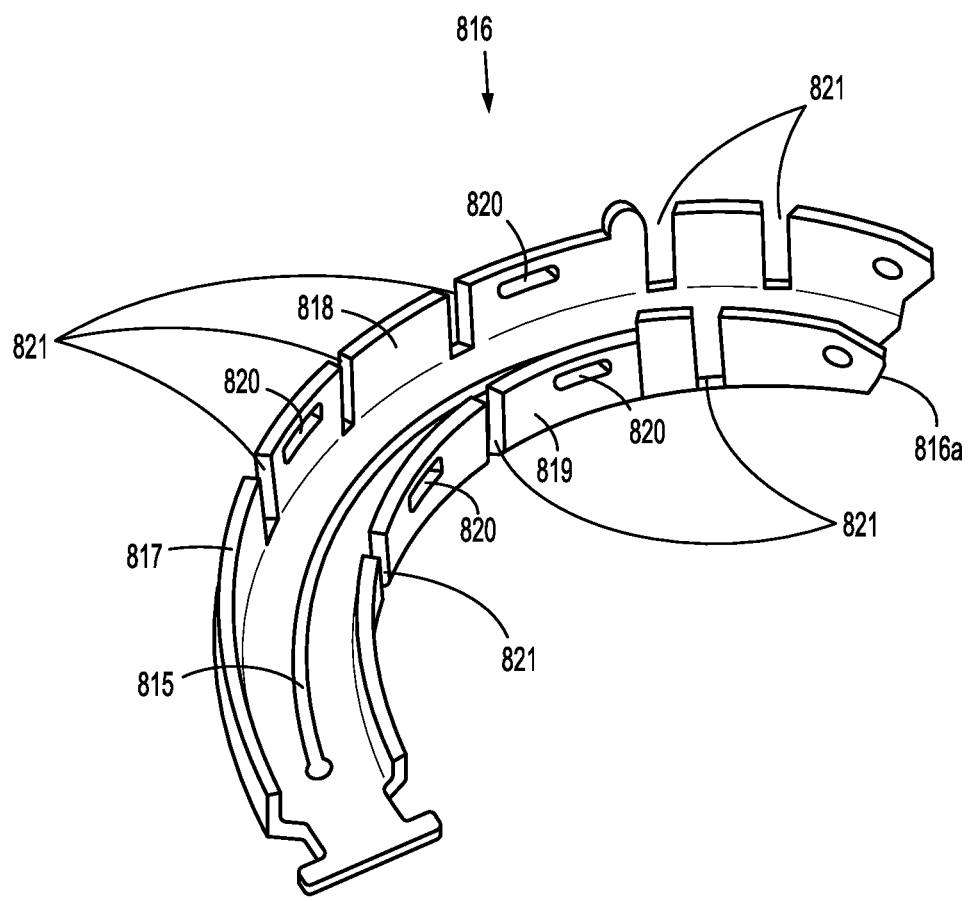
FIG. 33 is a perspective view of a carrier of a loading unit in accordance with an embodiment of the present disclosure.

With reference to FIG. 33, an alternate embodiment of curved channel or carrier 816 is shown. Carrier 816 is configured to receive and support longitudinally curved cartridge 518 (see FIG. 10), as discussed above. For example, cartridge 518 can be attached to carrier 816 by adhesives, a snap-fit connection, or other type of connection. In disclosed embodiments, the radius of curvature of carrier 816 is between about 1.00 inch and about 2.00 inches, and in particular, may be approximately 1.40 inches. Alternatively, carriers having other dimensions are envisioned, e.g., the radius of curvature may be greater than 2 inches or less than 1 inch. Cartridge 518 includes a pair of support struts 524 which rest on sidewalls 817 of carrier 816 to stabilize cartridge 518 on carrier 816. A proximal portion of carrier 816 includes an angled cam surface 816a which is positioned for engagement with lower beam 606c (FIG. 14) of clamping member 606 to facilitate pivoting of cartridge assembly 508 (including carrier 816) from the open position to the closed position. Carrier 816 also includes a slot 815 which is configured to allow projection 535 of actuation sled 536 to travel therethrough.

Carrier 816 includes a first or outer sidewall 818 and a second or inner sidewall 819. A plurality of notches 820 and a plurality of reliefs 821 are defined in outer and inner sidewalls 818 and 819. In the illustrated embodiment, each first sidewall 818 and second sidewall 819 includes two notches 820. It is envisioned that each first sidewall 818 and second sidewall 819 includes more or fewer notches 820. As illustrated, notches 820 are rectangular with rounded ends and extend completely through the respective sidewalls 818, 819. It is also envisioned that notches 820 can be differently sized, shaped, and/or positioned, and that at least one or all of notches 820 can extend partially through its respective sidewall 818, 819. Notches 820 are configured to accommodate protrusions or snap features formed on cartridge 518 to facilitate a snap-fit engagement between cartridge 518 and carrier 816.

In the illustrated embodiment of carrier 816, first sidewall 818 includes five reliefs 821, and second sidewall 819 includes three reliefs 821. As can be appreciated, each of first sidewall 818 and second sidewall 819 may include more or fewer reliefs 821. In the illustrated embodiment, reliefs 821 are generally rectangular sections removed from sidewalls 818, 819, and extend the entire height of sidewalls 818, 819. Alternatively, reliefs 821 may assume a variety of configurations and need not be rectangular. The inclusions of reliefs 821 facilitate the extrusion, drawing and/or bending of carrier 816 during manufacturing. For example, during a bending process, reliefs 821 allow for carrier 816 to compensate for the difference in the radius of curvature between outer sidewalls 818 and inner sidewalls 819.

The present disclosure also relates to a method of manufacturing carrier 816. The method includes combinations of cutting, bending, extruding and drawing sheet metal into the shape of carrier 816. As can be appreciated, the inclusion of reliefs 821 facilitates the manufacturing process by allowing the sheet metal to be bent into the desired shape. It is envisioned that the process or method of manufacturing carrier 816 involves fewer machining operations than manufacturing a different carrier, e.g., due to notches 820 and/or reliefs 821. For instance, it envisioned that manufacturing carrier 816, which includes notches 820 for accommodating a snap-fit relationship with cartridge 518, is more efficient than manufacturing a carrier with an inner groove for accommodating a snap-fit relationship with cartridge 518. That is, notches 820 can be created by the same machining operation (e.g., cutting) that is already being used to cut the desired shape out of the sheet metal, for example, as opposed to having to both cut and emplace a groove in the material, which may be otherwise required. Additionally, the design of carrier 816 does not require an increase sheet gauge of metal to be used; a standard gauge is usable to provide the necessary strength of carrier 816. As can be appreciated, these manufacturing advantages help to minimize waste, time, and cost of manufacturing a carrier for use in surgical stapling instrument 10 and/or loading unit 500.

It is further envisioned that the method of manufacturing carrier 816 consists of only cutting sheet metal into a first shape, and bending the sheet metal into a final shape. Other steps such as notching a groove in carrier 816 are not necessary because notches 820, which enable engagement between carrier 816 and cartridge 518, are created by the cutting operation. Grooves were previously required to enable engagement between a carrier and a cartridge, and required being separated notched. In this method, the cutting includes cutting at least one notch 820 (e.g., two notches 820) through a first curved side of the first shape, and cutting at least one notch 820 (e.g., two notches 820) through a second curved side of the first shape. The cutting may further include cutting at least one relief 821 (e.g., three reliefs 821) through the first curved side of the first shape, and cutting at least one relief 821 (e.g., three reliefs 821) through the second curved side of the first shape. Alternatively, any number of notches 820 and reliefs 821 can be provided to facilitate bending of carrier 816. It is disclosed that bending the sheet metal into a final shape includes bending the first curved side to form first sidewall 818, and bending the second curved side to create second sidewall 819.

Figures 34, 35:
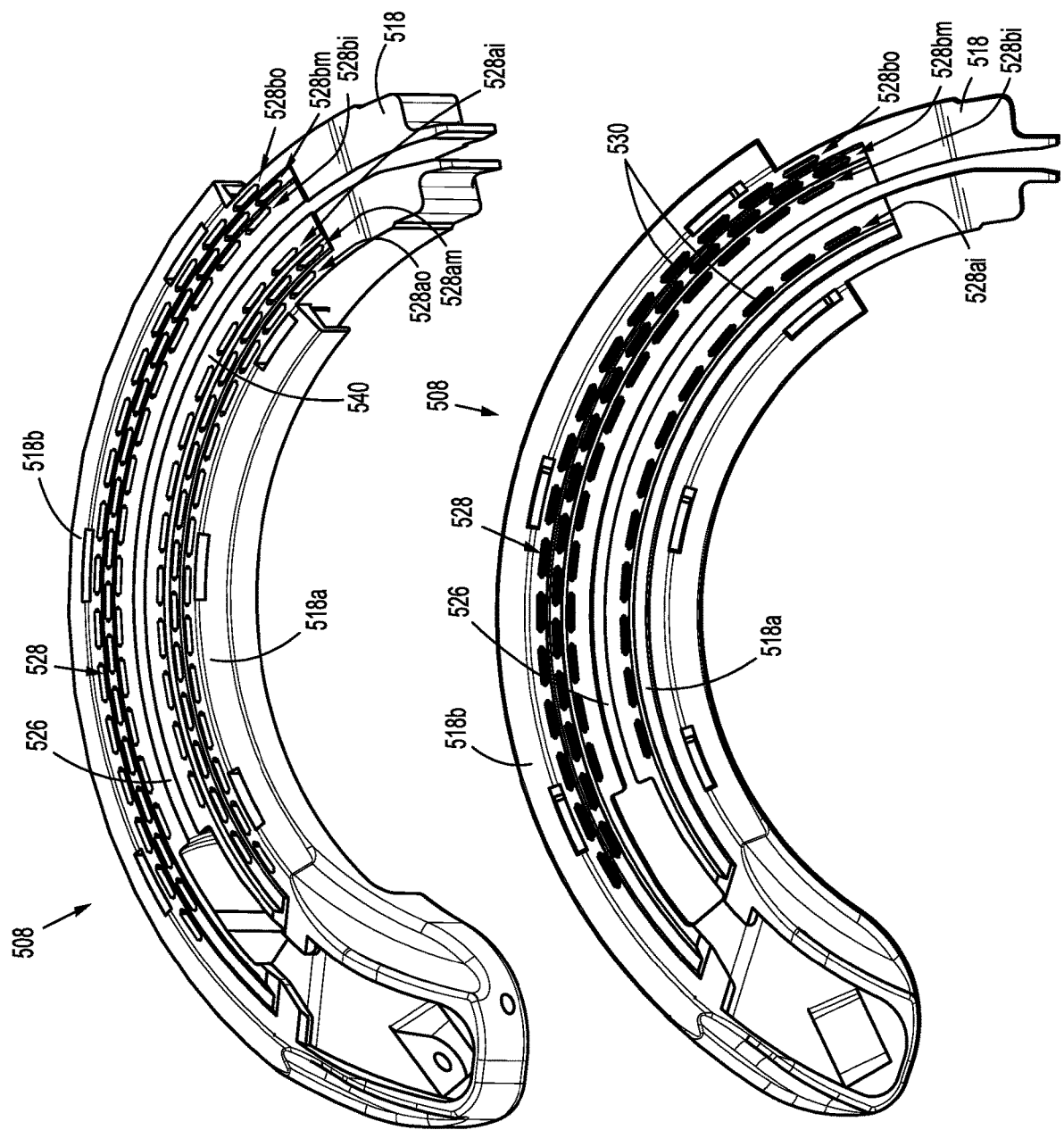
FIG. 34 is a perspective view of a cartridge assembly in accordance with embodiments of the present disclosure.
FIGS. 35-37 are cut-away views of the cartridge assembly of FIG. 34 schematically showing various positions of staples within slots of the cartridge assembly.

Referring now to FIGS. 34-37, cartridge assembly 508 is shown in accordance with embodiments of the present disclosure. With particular reference to FIG. 34, a cartridge assembly 508 including a cartridge 518 is illustrated having a plurality of slots 528 (e.g., staple retention slots) extending through corresponding openings in a tissue contacting surface 540 of cartridge 518. Additionally, cartridge 518 includes longitudinal channel 526 that is configured to allow dynamic clamping member 606 (FIG. 11) and a portion of drive assembly 560 (FIG. 32) to advance therethrough.

More specifically, each of an inner portion 518a (e.g., specimen side, shorter side) and an outer portion 518b (e.g., longer side) of cartridge 518 includes three rows of slots 528. That is, inner portion 518a of cartridge 518 includes an inner row 528ai of slots 528, a middle row 528am of slots 528 and an outer row 528ao of slots 528, and outer portion 508b of cartridge 518 includes an inner row 528bi of slots 528, a middle row 528bm of slots 528, and an outer row 528bo of slots 528. As shown, inner rows 528ai and 528bi of slots 528 are closer to longitudinal channel 526, and outer rows 528ao and 528bo of slots 528 are farther away from longitudinal channel 526.

Figures 36, 37:
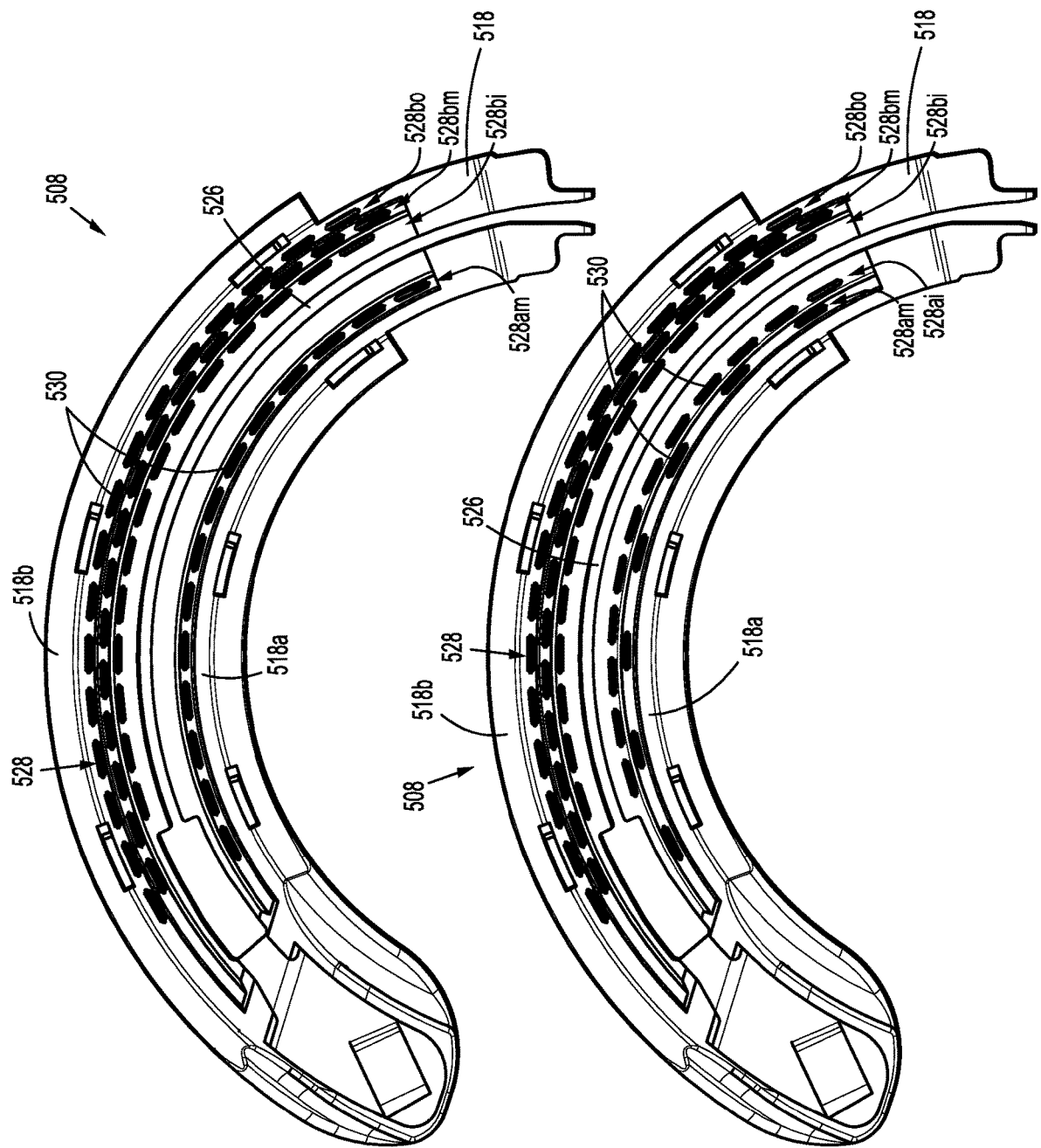

FIGS. 35-37 schematically illustrate different positions of staples 530 within slots 528. For clarity, the various slots 528 lacking a staple 530 therein are omitted in FIGS. 35-37; only slots 528 including a staple 530 therein are shown in FIGS. 35-37.

With particular reference to FIG. 35, each slot 528 of rows 528bi, 528bm, and 528bo of outer portion 508b of cartridge 518 is shown with a staple 530 therein, and slots 528 of inner row 528ai are shown with a staple 530 therein; slots 528 of middle row 528am and outer row 528ao lack staples 530.

With particular reference to FIG. 36, each slot 528 of rows 528bi, 528bm, and 528bo is shown with a staple 530 therein, and slots 528 of middle row 528am are shown with a staple 530 therein; slots 528 of inner row 528ai and outer row 528ao lack staples 530.

With particular reference to FIG. 37, each slot 528 of rows 528bi, 528bm, and 528bo is shown with a staple 530 therein, slots 528 of inner row 528ai are shown with a staple 530 therein, and alternating slots 528 of middle row 528am are shown with a staple 530 therein; slots 528 of outer row 528ao lack staples 530 and alternating slots 528 of middle row 528am lack staples 530.

That is, in the embodiments illustrated in FIGS. 35-37, each of the slots 528 on outer portion 518b of cartridge 518 includes a staple 530 therein, some slots 528 on inner portion 508a of cartridge 518 include a staple 530 therein, and some slots 528 on inner portion 508a of cartridge 518 lack a staple 530 therein. In addition to the illustrated embodiments, other embodiments are envisioned where one portion (e.g., inner portion 508a) of cartridge 518 includes fewer than three complete rows of slots 528 including staples 530. For example, it is envisioned that slots 528 of each row 528bi, 528bm, and 528bo include a staple 530 therein, and slots 528 of outer row 528ao include a staple 530 therein, while slots 528 of inner row 528ai and middle row 528am lack staples 530.

It is envisioned that the disclosed staple configurations facilitate pathological detection of clean margins after resection of diseased tissue. That is, such configurations help physicians view and/or sample tissue directly adjacent the cut line (i.e., along longitudinal channel 526) without interference from three rows of staples 530, for example. By contrast, in procedures where three complete rows of staples 530 are ejected on both sides of the cut line or longitudinal channel 526, it may be difficult for a physician or pathologist inspect and/or test the tissue adjacent the cut line to determine if that tissue includes any diseased tissue, which was intended to be removed during the surgical procedure. It is contemplated that the pathological detection and/or testing of the tissue can include detection and/or testing for cancerous cells. Additionally, while the embodiments illustrated in FIGS. 34-37 illustrate a curved cartridge assembly 508, it is envisioned that cartridge assembly 508 is linear (i.e., aligned with longitudinal axis "A-A" in FIG. 4).

The present disclosure also includes embodiments of cartridge assembly 508 having fewer than three complete rows of slots 528 on at least one side of longitudinal channel 526. Here, it is envisioned that each slot 528 includes a staple 530 therein. For example, it is envisioned that a cartridge assembly 508 of the present disclosure includes three complete rows of slots 528 on a first side of longitudinal channel 526, and includes two rows of slots 528 on a second side of longitudinal channel 526. Moreover, the present disclosure contemplates any combination of complete rows of slots 528 and partial rows of slots 528, with any or all of the slots 528 including a staple 530 therein.

Accordingly, the present disclosure includes a cartridge assembly 508 and/or a cartridge 518 having slots 528 including a plurality of staples 530 therein, and where several slots 528 (e.g., on inner side 508a of cartridge 518) are devoid of staples 530. Additionally, the present disclosure includes a loading unit 500 (FIG. 3) including cartridge assembly 508 and cartridge 518 including various configurations of slots 528 and staples 530, as described above, and a surgical instrument 10 including cartridge assembly 508 and cartridge 518 including various configurations of slots 528 and staples 530, as described above.

Further, the present disclosure includes methods of using surgical instrument 10, loading unit 500 (FIG. 3), cartridge assembly 508 and/or cartridge 518 including ejecting various configurations of staples 530, as described above. Additionally, the present disclosure relates to methods of performing a surgical procedure including ejecting various configurations of staples 530, as described above.

While the above description contains many specifics, these specifics should not be construed as limitations on the scope of the present disclosure, but merely as illustrations of various embodiments thereof. For example, the staple cartridge may have a flat tissue contacting surface, rather than a stepped surface. In any of the embodiments disclosed herein, all the staples can be the same size, or the surgical instrument can deploy two part fasteners. Embodiments disclosed herein can have different sized staples arranged in a variety of configurations. In any of the embodiments disclosed herein, the anvil may have a stepped surface, or may include different surfaces, and the staple cartridge can be stepped or flat. Therefore, the above description should not be construed as limiting, but merely as exemplifications of various embodiments. Those skilled in the art will envision other modifications within the scope and spirit of the claims appended hereto.

The invention claimed is:

1. A method of performing a surgical procedure, comprising:
   emplacing a first set of staples from a first side of a longitudinal channel of a surgical instrument in at least one row through tissue, wherein the first set of staples includes all of the staples on the first side of the longitudinal channel;
   emplacing a second set of staples from a second side of the longitudinal channel of the cartridge assembly in at least one row through tissue, wherein the second set of staples includes all of the staples on the second side of the longitudinal channel, wherein the first set of staples includes more staples than the second set of staples, wherein adjacent staples within the second set of staples are spaced a greater distance than adjacent staples within the first set of staples; and
   advancing a knife through the longitudinal channel to cut tissue.

2. The method according to claim 1, wherein emplacing the second set of staples includes emplacing the second set of staples in a single curved row through tissue.

3. The method according to claim 1, wherein the second set of staples includes fewer rows of staples than the first set of staples.

4. The method according to claim 1, further comprising pathological testing of a tissue remnant stapled by the second set of staples.

5. The method according to claim 4, wherein the pathological testing includes testing for cancer cells.

6. A method of performing a surgical procedure, comprising:
   emplacing a first set of fasteners from a first row of slots on a first side of a longitudinal channel of a cartridge assembly through tissue, wherein each slot in a second row of slots on the first side of the longitudinal channel is empty prior to emplacing the first set of fasteners; and
   emplacing a second set of fasteners from a third row of slots on a second side of the longitudinal channel of the surgical instrument through tissue.

7. The method according to claim 6, wherein each slot in the first row of slots includes a fastener disposed therein.

8. The method according to claim 6, wherein each slot in the third row of slots includes a fastener disposed therein.

9. The method according to claim 6, wherein the first side of the longitudinal channel includes three rows of slots.

10. The method according to claim 9, wherein the second side of the longitudinal channel includes three rows of slots.

11. The method according to claim 10, wherein each row of slots of the three rows of slots on the second side of the longitudinal channel includes at least one slot having a fastener disposed therein.

12. The method according to claim 11, wherein each row of slots of the three rows of slots on the first side of the longitudinal channel includes at least one empty slot.

13. The method according to claim 6, wherein the cartridge assembly defines a radius of curvature of between about 1 inch and about 2 inches.

14. The method according to claim 13, wherein the first side of the longitudinal channel is shorter than the second side of the longitudinal channel.

* * * * *